US007825097B2

(12) United States Patent
Davis et al.

(10) Patent No.: US 7,825,097 B2
(45) Date of Patent: Nov. 2, 2010

(54) NUCLEOTIDE VECTOR VACCINE FOR IMMUNIZATION AGAINST HEPATITIS

(75) Inventors: Heather Lynn Davis, Dunrobin (CA); Robert Gerald Whalen, Foster City, CA (US); Marie-Louise Michel, Paris (FR)

(73) Assignees: Institut Pasteur, Paris (FR); Institut National de la Sante et de la Recherche Medicale, Paris (FR); Universite d'Ottawa, Ottawa (CA)

( * ) Notice: Subject to any disclaimer, the term of this patent is extended or adjusted under 35 U.S.C. 154(b) by 740 days.

(21) Appl. No.: 10/644,267

(22) Filed: Aug. 20, 2003

(65) Prior Publication Data
US 2005/0042203 A1 Feb. 24, 2005

Related U.S. Application Data

(63) Continuation of application No. 09/146,072, filed on Sep. 2, 1998, now Pat. No. 6,635,624, which is a continuation of application No. 08/633,821, filed on Aug. 2, 1996, now abandoned.

(51) Int. Cl.
A01N 43/04 (2006.01)
A61K 31/70 (2006.01)
C12N 15/00 (2006.01)
(52) U.S. Cl. .................................. 514/44 R; 435/320.1
(58) Field of Classification Search .................... 514/44
See application file for complete search history.

(56) References Cited

U.S. PATENT DOCUMENTS

| 565,203 | A | 8/1896 | Gluck et al. |
|---|---|---|---|
| 4,547,367 | A | 10/1985 | Tabor et al. |
| 4,592,742 | A | 6/1986 | Landau |
| 4,710,463 | A | 12/1987 | Murray et al. |
| 4,803,164 | A | 2/1989 | Hitzeman et al. |
| 4,839,277 | A | 6/1989 | Sugahara et al. |
| 4,957,869 | A | 9/1990 | Arnot et al. |
| 5,019,386 | A | 5/1991 | Machida et al. |
| 5,256,553 | A | 10/1993 | Overell et al. |
| 5,256,767 | A | 10/1993 | Salk et al. |
| 5,565,203 | A | 10/1996 | Glück et al. |
| 5,593,972 | A | 1/1997 | Weiner et al. |
| 5,620,896 | A | 4/1997 | Herrmann et al. |
| 5,643,578 | A | 7/1997 | Robinson et al. |
| 5,679,647 | A | 10/1997 | Carson et al. |
| 5,714,316 | A | 2/1998 | Weiner et al. |
| 5,736,524 | A | 4/1998 | Content et al. |
| 5,780,448 | A | 7/1998 | Davis |
| 5,786,189 | A | 7/1998 | Locht et al. |
| 5,804,566 | A | 9/1998 | Carson et al. |
| 5,814,617 | A | 9/1998 | Hoffman et al. |
| 5,817,637 | A | 10/1998 | Weiner et al. |
| 5,830,876 | A | 11/1998 | Weiner et al. |
| 5,830,877 | A | 11/1998 | Carson et al. |
| 5,856,462 | A | 1/1999 | Agrawal |
| 5,972,346 | A | 10/1999 | Hauser et al. |
| 5,981,274 | A | 11/1999 | Tyrrell et al. |
| 5,985,847 | A | 11/1999 | Carson et al. |
| 6,635,624 | B1 | 10/2003 | Davis et al. |
| 2002/0142978 | A1 | 10/2002 | Raz et al. |
| 2002/0192184 | A1 | 12/2002 | Carpentier |

FOREIGN PATENT DOCUMENTS

| CA | 1 169 793 | 6/1984 |
|---|---|---|
| EP | 0 156 712 A1 | 10/1985 |
| EP | 0 185 573 A1 | 6/1986 |
| WO | WO 88/06185 A1 | 8/1988 |
| WO | WO 90/11092 A1 | 10/1990 |
| WO | WO 92/06212 A1 | 4/1992 |
| WO | WO 93/09236 A1 | 5/1993 |
| WO | WO 93/15207 A1 | 8/1993 |
| WO | WO 93/17111 A1 | 9/1993 |
| WO | WO 95/05853 A1 | 3/1995 |
| WO | WO 93/11307 A1 | 4/1995 |
| WO | WO-9728259 A1 | 8/1997 |
| WO | WO-2005004910 A2 | 1/2005 |
| WO | WO-2005039633 A1 | 5/2005 |

OTHER PUBLICATIONS

Babiuk et al. (2003) Induction of immune responses by DNA vaccines in large animals. Vaccine 21: 649-658.*
Ertl et al. (1996) Genetic immunization. Viral Immunology 9(1): 1-9.*
Davis et al., Chapter 18: DNA-based immunization. in Molecular and Cell Biology of Human Gene Therapeutics. George Dickson, ed., 1995: p. 368-87. (ISBN: 0 412 62550 4).
Hahm et al., Efficacy of polyadenylic.polyuridylic acid in the treatment of chronic active hepatitis B. Int J Immunopharmacol. Mar. 1994;16(3):217-25.
Liu et al., Immunization of non-human primates with DNA vaccines. Vaccine. Jun. 1997;15(8):909-12.
Michel et al., DNA-mediated immunization to the hepatitis B surface antigen in mice: aspects of the humoral response mimic hepatitis B viral infection in humans. Proc Natl Acad Sci U S A. Jun. 6, 1995;92(12):5307-11.
Staats et al., Mucosal immunity to infection with implications for vaccine development. Curr Opin Immunol. Aug. 1994;6(4):572-83. Review.

(Continued)

Primary Examiner—Anne-Marie Falk
(74) Attorney, Agent, or Firm—Wolf, Greenfield & Sacks, P.C.; Gregg C. Benson

(57) ABSTRACT

Nucleotide vector comprising at least one gene or one complementary DNA coding for at least a portion of a virus, and a promoter providing for the expression of such gene in muscle cells. The gene may be the S gene of the hepatitis B virus.

A vaccine preparation containing said bare DNA is injected into the host previously treated with a substance capable of inducing a coagulating necrosis of the muscle fibres.

16 Claims, 12 Drawing Sheets

OTHER PUBLICATIONS

Alpar et al., Potential of particulate carriers for the mucosal delivery of DNA vaccines. Biochem Soc Trans. May 1997;25(2):337S.

Branda et al., Immune stimulation by an antisense oligomer complementary to the rev gene of HIV-1. Biochem Pharmacol. May 25, 1993;45(10):2037-43.

Calarota et al., Cellular cytotoxic response induced by DNA vaccination in HIV-1-infected patients. Lancet. May 2, 1998;351(9112):1320-5.

Chen et al., Protective immunity induced by oral immunization with a rotavirus DNA vaccine encapsulated in microparticles. J Virol. Jul. 1998;72(7):5757-61.

Daheshia et al., Immune induction and modulation by topical ocular administration of plasmid DNA encoding antigens and cytokines. Vaccine. Jul. 1998;16(11-12):1103-10.

Davis et al., Plasmid DNA expression systems for the purpose of immunization. Curr Opin Biotechnol. Oct. 1997;8(5):635-46.

Etchart et al., Class I-restricted CTL induction by mucosal immunization with naked DNA encoding measles virus haemagglutinin. J Gen Virol. Jul. 1997;78 ( Pt 7):1577-80.

Fields et al., Fields' Virology. 2001;1:1153.

Gallichan et al., Specific secretory immune responses in the female genital tract following intranasal immunization with a recombinant adenovirus expressing glycoprotein B of herpes simplex virus. Vaccine. Nov. 1995;13(16):1589-95.

Geissler et al., Enhancement of cellular and humoral immune responses to hepatitis C virus core protein using DNA-based vaccines augmented with cytokine-expressing plasmids. J Immunol. Feb. 1, 1995;158(3):1231-7.

Gramzinski et al., Immune response to a hepatitis B DNA vaccine in Aotus monkeys: a comparison of vaccine formulation, route, and method of administration. Mol Med. Feb. 1998;4(2):109-18.

Halperin et al., A phase I study of the safety and immunogenicity of recombinant hepatitis B surface antigen co-administered with an immunostimulatory phosphorothioate oligonucleotide adjuvant. Vaccine. Jun. 2003 2;21(19-20):2461-7.

Halperin et al., Comparison of the safety and immunogenicity of hepatitis B virus surface antigen co-administered with an immunostimulatory phosphorothioate oligonucleotide and a licensed hepatitis B vaccine in healthy young adults. Vaccine. Jan. 9, 2006;24(1):20-6. Epub Sep. 12, 2005. Abstract Only.

Hedley et al., Microspheres containing plasmid-encoded antigens elicit cytotoxic T-cell responses. Nat Med. Mar. 1998;4(3):365-8.

Jones et al., Poly(DL-lactide-co-glycolide)-encapsulated plasmid DNA elicits systemic and mucosal antibody responses to encoded protein after oral administration. Vaccine. Jun. 1997;15(8):814-7.

Klinman et al., Therapeutic applications of CpG-containing oligodeoxynucleotides. Antisense Nucleic Acid Drug Dev. Apr. 1998;8(2):181-4.

Leclerc et al., The preferential induction of a Th1 immune response by DNA-based immunization is mediated by the immunostimulatory effect of plasmid DNA. Cell Immunol. Aug. 1, 1997;179(2):97-106.

Lee et al., Immuno-stimulatory effects of bacterial-derived plasmids depend on the nature of the antigen in intramuscular DNA inoculations. Immunology. Jul. 1998;94(3):285-9.

MacGregor et al., First human trial of a DNA-based vaccine for treatment of human immunodeficiency virus type 1 infection: safety and host response. J Infect Dis. Jul. 1998;178(1):92-100.

McCluskie et al., Novel strategies using DNA for the induction of mucosal immunity. Crit Rev Immunol. 1999;19(4):303-29.

McCluskie et al., Novel adjuvant systems. Curr Drug Targets Infect Disord. Nov. 2001;1(3):263-71.

McCuskie et al., Mucosal immunization with DNA vaccines. Microbes Infect. Jul. 1999;1(9):685-98.

McCluskie et al., The role of CpG in DNA vaccines. Springer Semin Immunopathol. 2000;22(1-2):125-32.

McCluskie et al., Route and method of delivery of DNA vaccine influence immune responses in mice and non-human primates. Mol Med. May 1999;5(5):287-300.

Payette et al., History of vaccines and positioning of current trends. Curr Drug Targets Infect Disord. Nov. 2001;1(3):241-7.

Roman et al., Immunostimulatory DNA sequences function as T helper-1-promoting adjuvants. Nat Med. Aug. 1997;3(8):849-54.

Rubanyi, The future of human gene therapy. Mol Aspects Med. Jun. 2001;22(3):113-42.

Tacket et al., Phase 1 safety and immune response studies of a DNA vaccine encoding hepatitis B surface antigen delivered by a gene delivery device. Vaccine. Jul. 16, 1999;17(22):2826-9.

Ugen et al., DNA vaccination with HIV-1 expressing constructs elicits immune responses in humans. Vaccine. Nov. 1998;16(19):1818-21.

Wang et al., Induction of antigen-specific cytotoxic T lymphocytes in humans by a malaria DNA vaccine. Science. Oct. 16, 1998;282(5388):476-80.

Weeratna et al., Reduction of antigen expression from DNA vaccines by coadministered oligodeoxynucleotides. Antisense Nucleic Acid Drug Dev. Aug. 1998;8(4):351-6.

Weeratna et al., CpG DNA induces stronger immune responses with less toxicity than other adjuvants. Vaccine. Mar. 6, 2000;18(17):1755-62.

Abbas et al., Cellular and Molecular Biology. 1991: pp. 4 and 5.

Catanzaro, et al. Phase I clinical evaluation of a six-plasmid multiclade HIV-1 DNA candidate vaccine. Vaccine. 2007; 25: 4085-92.

Davis et al., Direct gene transfer in skeletal muscle: plasmid DNA-based immunization against the hepatitis B virus surface antigen. Vaccine. Dec. 1994;12(16):1503-9.

Ferrari et al., Cellular immune response to hepatitis B virus-encoded antigens in acute and chronic hepatitis B virus infection. J Immunol. Nov. 15, 1990;145(10):3442-9.

Mancini-Bourgine, et al., Induction or expansion of T-cell responses by a hepatitis B DNA vaccine administered to chronic HBV carriers. Hepatology 2004; 40: 874-82.

Trepo et al., Diagnostic markers of viral hepatitis B and C. Gut. 1993;34(2 Suppl):S20-5.

Whalen et al., DNA vaccines for emerging infectious diseases: what if? Emerg Infect Dis. Jul.-Sep. 1996;2(3):168-75. Abstract Only.

Yang, et al., Correlation of antiviral T-Cell responses with suppression of viral rebound in chronic hepatitis B carriers: a proof-of-concept study. Gene Therapy. 2006; 13: 1110-17.

Yokosuka et al., Detection and direct sequencing of hepatitis B virus genome by DNA amplification method. Gastroenterology. Jan. 1991;100(1):175-81.

Ferrari et al., Cellular immune response to hepatitis B virus-encoded antigens in acute and chronic hepatitis B virus infection. The Journal of Immunology, 145(10): 3442-3449, (1990).

Kuhöber et al., DNA immunization induces antibody and cytotoxic T cell responses to hepatitis B core antigen in H-$2^b$ mice. The Journal of Immunology, 1996, 156:3687-3695.

Kuhrober et al., Dna vaccination with plasmids encoding the intracellular (HBcAg) or secreted (HBeAg) form of the core protein of hepatitis B virus primes T cell responses to two overlapping Kb- and Kd —restricted epitopes. International Immunology, 1997, 9(8): 1203-1212.

Lee et al., Immune response induced by immunization with Hepatitis B virus core DNA isolated from chronic active hepatitis patients. Immunology Letters. 2001;78:13-20.

Lu et al., Immunization of Woodchucks with plastmids expressing woodchuck hepatitis virus (WHV) core antigen and surface antigen suppresses WHV infection. Journal of Virology. Jan. 1999; 73(1):281-289.

Mancini et al., DNA-based immunization against the envelope proteins of the hepatitis B virus. Journal of Biotechnology. 1996; 44:47-57.

Mancini-Bourgine et al., Immunogenicity of a hepatitis B DNA vaccine administered to chronic HBV carriers. Vaccine, 2006, 24:4482-4489.

Triyatni et al., Protective efficacy of DNA vaccines against duck hepatitis B virus infection. Journal of Virology, Jan. 1998; 72(1):84-94.

[No Author Listed] Diagram and sequence of GenBank retrieved sequence equivalent to fragment carrying the HSV TK gene in Kit et al., 1980 Nucl Acid Res 8(22):5233-53.

[No Author Listed] Sequence of Hepatitis B S antigen gene fragment present in construct of Crowley et al. (1983) Molecular and Cellular Biology, vol. 3(1):44-55.

Abruzzese et al., Ligand-dependent regulation of vascular endothelial growth factor and erythropoietin expression by a plasmid-based autoinducible geneswitch system. Mol Ther. Sep. 200;2(3):276-87.

Bos et al., Cationic polymers that enhance the performance of HbsAg DNA in vivo. Vaccine. Dec. 9, 2004;23(4):460-9.

Chen et al., [Construction of HBV S gene recombinant and its immunity induced in mice]. Zhejiang Da Xue Xue Bao Yi Xue Ban. Aug. 2002;31(6):440-443. Chinese.
Cheng et al. In vivo promoter activity and transgene expression in mammalian somatic tissues evaluated by using particle bombardment. Proc Natl Acad Sci U S A. May 15, 1993;90(10):4455-9.
Cox et al., Bovine herpesvirus 1: immune responses in mice and cattle injected with plasmid DNA. J. Virol. Sep. 1993;67(9):5664-7.
Crowley et al., Plasmid-directed synthesis of hepatitis B surface antigen in monkey cells. Mol. Cell Biol. Jan. 1983;3(1):44-55.
Davis et al., DNA-mediated immunization to hepatitis B surface antigen: longevity of primary response and effect of boost. Vaccine. Jun. 1996;14(9):910-5.
Iwarson et al., Protection against hepatitis B virus infection by immunization with hepatitis B core antigen. Gastroenterology. Mar. 1985;88(3):763-7.
Jazayeri et al., HBV core sequence: definition of genotype-specific variability and correlation with geographical origin. J. Viral Hepat. Nov. 2004;11(6):488-501.
Kim et al., Induction of immunity against hepatitis B virus surface antigen by intranasal DNA vaccination using a cationic emulsion as a mucosal gene carrier. Mol Cells. Oct. 31, 2006;22(2):175-81. Abstract only.
Mancini et al., DNA-mediated immunization in a transgenic mouse model of the hepatitis B surface antigen chronic carrier state. Proc Natl Acad Sci U S A. Oct. 29, 1996;93(22):12496-501.
Menne et al., The woodchuck as an animal model for pathogenesis and therapy of chronic hepatitis B virus infection. World J Gastroenterol. Jan. 7, 2007;13(1):104-24.
Michel et al., Induction of anti-human immunodeficiency virus (HIV) neutralizing antibodies in rabbits immunized with recombinant HIV—hepatitis B surface antigen particles. Proc Natl Acad Sci U S A. Nov. 1988;85(21):7957-61.
Milich et al., Antibody production to the nucleocapsid and envelope of the hepatitis B virus primed by a single synthetic T cell site. Nature. Oct. 8-14, 1987;329(6139):547-9.
Murray et al., Protective immunisation against hepatitis B with an internal antigen of the virus. J Med Virol. Oct. 1987;23(2):101-7.
Samanta et al., Expression of hepatitis B virus surface antigen containing the pre-S region in mammalian cell culture system. Vaccine. Feb. 1989;7(1):69-76.
Schlienger et al., Human immunodeficiency virus type 1 major neutralizing determinant exposed on hepatitis B surface antigen particles is highly immunogenic in primated. J. Virol. Apr. 1992;66(4):2570-6.
Siddiqui et al., Expression of the hepatitis B virus X gene in mammalian cells. Proc Natl Acad Sci U S A. Apr. 1987;84(8):2513-7.
Simonsen et al., Analysis of processing and polyadenylation signals of the hepatitis B virus surface antigen gene by using simian virus 40-hepatitis B virus chimeric plasmids. Mol Cell Biol. Dec. 1983;3(12):2250-8.
Wells, Improved gene transfer by direct plasmid injection associated with regeneration in mouse skeletal muscle. FEBS Lett. Oct. 1993;332(1-2):179-82.
Zelenin et al., Bacterial beta-galactosidase and human dystrophin genes are expressed in mouse skeletal muscle fibers after ballistic transfection. FEBS Lett. Sep. 8, 1997;414(2):319-22.
Agrawal, S., et al., "Pharmacokinetics of Antisense Oligonucleotides", *Clin Pharmacokinet*., 7-16, (1995).
Cattaneo, R., et al., "Signals regulating hepatitis B surface antigen transcription", *Nature*, 305:336-338, (1983).
Cowdery, J., et al., "Bacterial DNA Induces NK Cells to Produce IFN-γ In Vivo and Increases the Toxicity of Lipopolysaccharides" *Bacterial DNA*. . . , (1996).
Davis, H.,et al., "Direct gene transfer into skeletal muscle in vivo: Factors affecting efficiency of transfer and stability of expression" *Human Gene Therapy*, 4: 151-159, (1993).
Davis, H.,et al., "DNA-based immunization induces continuous secretion of hepatitis B surface antigen and high levels of circulating antibod" *Human Molecular Genetics*, 2:1847-1852, (1993).
Davis, H.,et al., DNA vaccine for hepatitis B: Evidence for immunogenicity in chimpanzees and comparison with other vaccines, *Proc Natl Acad, Sci*, 93:7213-7218, (1996).
Fujieda, S., et al., "Effect of OK-432 on Cytotoxic Activity in Cancer patients without Tumor Burden", *Anticancer Research*, 12:1941-1946, (1992).
Fujisawa T et al, "Serial changes in titers of antibody to hepatitis B surface antigen after immunization of infants born to mothers with hepatitis B e antigen". *Pediatr. Gastroenterol Nutr*, 23:270-274, (1996).
Fuller, D., et al., "Induction of immunodeficiency virus-specific immune responses in rhesus monkeys following gene Gun-mediated DNA vaccination", *J. Med. Primates*, 25:236-241, (1996).
Fynan, E., et al., "DNA vaccines: Protective immunizations by parentaeral, mucosal, and gene-gun inoculations", *Proc. Natl. Acad. Sci*., 90:11478-11482, (1993).
Gao, W., et al., "Phosphorothioate Oligonucleotides are inhibitors of human DNA polymerases and Rnase H: implications for antisense techology", 223-229, (1991).
Jones, T., et al., "Synthetic oligodeoxynucleotiedes containing CpG motifs enhance immunogenicity of a peptide malaria vaccine in Aotus monkeys", *Vaccine*, 17:3065-3071, (1999).
Karlin, S., et al., "Why is CpG Suppressed in the Genomes of Virtually All Small Eukaryotic Viruses but Not in Those of large Eukaryotic Virues?", Journal of Virology, 2889-2897, (1994).
Kataoka, T., et al., "Antitumor Activity of Synthetic Oligonucleotides with Sequences from cDNA Encoding Proteins of Mycbacterium vobis BCG", Jpn. J. Cancer Res., 83:244-247, (1992).
Krieg, A., et al., "CpG motifs in bacterial DNA trigger direct B-cell activation", Nature, 374:546-549, (1995).
Lee, Pi., et al., "Long-term efficacy of recombinant hepatitis B vaccine and risk of natural infection in infants born to mothers with hepatitis B e antigen." *J. Pediatr*, 126: 716-721, (1995).
Li, Z., et al., "Desmin sequence elements regulating skeletal muscle-specific expression in transgenic mice", *Development*, 117:947-959, (1993).
Liu, H., et al., "Immunostimulatory CpG Oligodeoxynucleotides Enhance the Immune Response to Vaccine Strategies Involving Granulocyte-Machrophate colony-Stimulating Factor", *Blood*, 92:10:3730-3736, (1998).
Lutynski R. and Juszczyk R, "The level of anti-HBs in blood serum of persons selected from a group of Krakow inhabitants" *Folia Med. Cracov*., 38: 63-68, (1997).
Mcintyre, K., et al., "A Sense Phosphorothioate Oligonucleotide Directed to the Initiation Codon of Transcription Factor NF-kB p65 Causes Sequence-Specific Immune Stimulation", *Antisense & Nucleic Acid Drug Development*, 3:309-322, (1993).
Manzel, L., et al., "Lack of Immune Stimulation by Immobilized CpG-Oligodeoxynucleotide", *Antisense&Nucleic Acid Drug Development*, 9:459-464, (1999).
Mojcik, C., et al., "Administration of a Phosphorothioate Oligonucleotide Antisense Murine Endogenous Retroviral MCF env Causes Immune Effects in Vivo in a Sequence-Specific Manner", *Clinical Immunology and ImmunoPathology*, 67:2:130-136, (1993).
Pisetsky, D., et al., "Immunologic Consequences of Nucleic Acid Therapy", *Antisense&Nucleic Acid Drug Development*, 5:219-225, (1995).
Prince, A., et al., "Successful nucleic acid based immunization of newborn chimpanzees against hepatitis B virus", *Vaccine*, 15:8:916-919, (1997).
Raz, E.,et al., "Intradermal gene immunization: The possible role of DNA utake in the induction of cellular immunity to viruses", *Proc. Natl. Acad. Sci*., 91:9515-9523, (1994).
Robinson, H., "Nucleic acid vaccines: an overview", *Vaccine*, 15:8:785-787 , (1997).

Sands, H., et al., "Biodistribution and Metabolism of Internally 3H-Labeled Oligonucleotides. I. Comparison of a Phosphodiester and a Phosphorothioate", *The American Society for Pharmacology*, 45:932-943, (1994).

Stein, C., et al., "Antisense Oligonucleotides as Therapeutic Agents—Is the bullet Really Magical", Science, 261:1004-1012, (1993).

Thomsen, D., et al., "Promoter-regulatory region of the major immediate early gene of human cytomegalovirus", *Proc. Natl. Acad. Sci.*, 81:659-663, (1984).

Tokunaga, T., et al., "Antitumor Activity of Deoxyribonucleic Acid Fraction From Mycobacterium bovis BCG. I. Isolation, Physicochemical Characterization, and Antitumor Activity", JNCI, 72:955-962, (1984).

Ulmer, J., et al., "Heterologous protection Against Influenza by Injection of DNA Encoding a Viral Protein", *Science*, 259:1745-1749, (1993).

Valenzuela, P., et al., "Synthesis and assembly of hepatitis B virus surface antigen particles in yeast", *Nature*, 298:347-350, (1982).

Wang, B., et al., "Gene inoculation generates immune responses against human immunodeficiency virus type 1", *Proc Natl. Acad Sci.*, 90:4156-4160, (1993).

Yaswen, P., et al., "Effects of Sequences of Thioated Oligonucleotides on cultured Human Mammary Epithelial Cells", *Antisense Research and Development*, 3:67-77, (1993).

Zelphati, O., et al., Inhibition of HIV-1 Replication in Cultured Cells with Antisense Oligonucleotides Encapsulated in Immunoliposomes, *Antisense Research and Development*, 3:323-338, (1993).

Calandra, G.B. et al., Recommendations for Prevention of Hepatitis B with Vaccine, Hepatitis B Vaccines in Clinical Practice, Merck Research Laboratories, pp. 1-16, 1993.

Chambon, P., ADN: sur la piste du vaccine génétique, *Sciences et Avenir*, Sep. 1993, pp. 22-25.

Hayes, J.R. et al., Particle-mediated nucleic acid immunization, Journal of Biotechnology 44, 1996, pp. 37-42.

Kuhöber, A., et al. DNA Immunization Induces Antibody and Cytotoxic T Cell Responses to Hepatitis B Core Antigen in H-$2^b$ Mice, *The American Association of Immunologists*, 1996, pp. 3687-3695.

Leborgne, S. et al., In Vivo Induction of Specific Cytotoxic T Lymphocytes in Mice and Rhesus Macaques Immunized with DNA, (Jan. 1998) Virology 240(2).

Vector Encoding an HIV Epitope Fused with Hepatitis B Surface Antigen, *Virology* 240, 304-315, 1998, Article No. VY978942.

Wolff et al., Direct Gene Transfer into Muse Muscle in Vivo, Science, vol. 247, Mar. 1990, pp. 1465-1468.

Raz, E. et al., "Systemic immunological effects of cytokine genes injected into skeletal muscle", *Proc. Natl. Acad. Sci. USA*, May 1993, pp. 4523-4527, vol. 90.

Tang, D. et al., "Genetic immunization is a simple method for eliciting an immune response", *Nature*, Mar. 12, 1992, pp. 152-154, vol. 356.

Chattergoon et al., Genetic Immunization: A New Era in Vaccines and Immune Therapeutics, FASEB Journal, vol. 11, pp. 753-763, (1997).

* cited by examiner

NUCLEOTIDE VECTOR VACCINE FOR IMMUNIZATION AGAINST HEPATITIS

RELATED APPLICATIONS

This application is a continuation of U.S. patent application Ser. No. 09/146,072, filed Sep. 2, 1998, now U.S. Pat. No. 6,635,624, which is a continuation of U.S. application Ser. No. 08/633,821, filed Aug. 2, 1996, now abandoned, which claims priority to which claims priority to PCT/FR94/00483, filed Apr. 27, 1994 (French Patent Application No. 93/12659, filed Oct, 22, 1993), each of which are incorporated herein by reference in their entirety.

The present application relates to a vector for immunization against hepatitis.

It is also related to a composition containing this vector.

Immunization by injection of bare DNA into muscle tissues has been the object of several studies since the beginning of the 1990s.

Thus, ULMER et al. (Science, 259, 1745-1749, 1993) obtained protection against the Influenza virus by induction of the cytotoxic T lymphocytes through injection of a plasmid coding for the Influenza A nucleoprotein into the quadriceps of mice. The plasmid used carries either the Rous sarcoma virus promoter or the cytomegalo virus promoter.

RAZ et al. (Proc. Natl. Acad. Sci. USA, 90, 4523-4527, 1993) injected vectors comprising the Rous sarcoma virus promoter and a gene coding for interleukin-2, interleukin-4 or the β1-type transforming growth factor (TGF-β1). The humoral and cell immune responses of the mice to which these plasmids have been intramuscularly administered are improved.

WANG et al. (Proc. Natl. Acad. Sci. USA, 90, 4156-4160, 1993) injected a plasmid carrying a gene coding for the envelope protein of the HIV-1 virus into mice muscles. The plasmid injection was preceded by treatment with bupivacaine in the same area of the muscle. The authors demonstrate the presence of antibodies capable of neutralizing the HIV-1 virus infection. However, it will be noted that DNA was injected twice a week for a total of four injections.

DAVIS et al. (Compte-Rendu du 28ème Congrès Européen sur le muscle, Bielefeld, Germany, 21-25 September 1992) injected plasmids carrying a luciferase or β-galactosidase gene coding by pretreating the muscles with sucrose or a cardiotoxin. The authors observed the expression of luciferase or β-galactosidase.

More recently, an article published in Science et Avenir (September 1993, pages 22-25) indicates that WHALEN et DAVIS succeeded in immunizing mice against the hepatitis B virus by injecting pure DNA from the virus into their muscles. An initial injection of snake venom toxin, followed 5 to 10 days later by a DNA injection, is generally cited. It is specified that this is not a practical method.

These studies were preceded by other experiments in which various DNAs were injected, in particular into muscle tissues. Thus, the PCT/US application No. 90/01 515 (published under N° WO-90/11 092) discloses various plasmid constructions which can be injected in particular into muscle tissues for the treatment of muscular dystrophy. However, this document specifies that DNA is preferentially injected in liposomes.

This also applies to Canadian patent CA-362.966 (published under N° 1.169.793) which discloses the intramuscular injection of liposomes containing DNA coding in particular for HBs and HBc antigens. The results described in this patent mention the HBs antigen expression. The presence of anti-HBs antibodies was not investigated.

International application PCT/FR 92/00 898 (published under N° WO-93/06 223) discloses viral vectors which can be conveyed to target cells by blood. These vectors are thus recognized by the cell receptors, such as the muscle cells, and can be used in the treatment of muscular dystrophy or of thrombosis.

This application does not relate to immunization against viruses such as, for example, that of hepatitis B.

Thus, it arises from the state of the art cited that although immunization techniques against hepatitis by injection of bare DNA are already known, these techniques had many disadvantages which made their implementation impractical.

Furthermore, the bare DNA used to vaccinate the mice was pure DNA from the virus. This type of treatment can not be considered for human vaccination due to the risks involved for the patients.

Finally, the earliest experiments in which the injected DNA is contained in liposomes did not demonstrate any immune response.

The applicant has therefore aimed at discovering new vector constructions allowing immunization against hepatitis without having a detrimental effect on human health.

He has further aimed at finding an additive for compositions containing the constructions which would allow an effective degeneration of muscle tissue before the DNA injection, and compatible with the requirements of human health.

The applicant has surprisingly shown that it is possible to achieve an effective and durable level of antibodies much greater than the level permitting to obtain in man an efficient and durable immune protection against infection by the hepatitis virus, by administering by intramuscular injection a vector with defined construction, and a substance capable of inducing a coagulating necrosis of the muscle fibres.

The present application thus relates to a nucleotide vector comprising at least:

a gene or a complementary DNA coding for at least a part of the virus protein, and a promoter allowing the expression of this gene in muscle cells.

Said vector may not replicate in these cells.

It may also be replicative, allowing to obtain a high number of copies per cell and to enhance the immune response.

The vector is also chosen in order to avoid its integration into the cell's DNA, such integrations being known to activate the oncogens and induce cell canceration.

The vector according to the present invention is advantageously a plasmid of partly bacterial origin and notably carrying a bacterial replication origin and a gene allowing its selection, such as a gene for resistance to an antibiotic.

This vector may also be provided with a replication origin allowing it to replicate in the muscle cells of its host, such as the replication origin of the bovine papilloma virus.

The gene or the complementary DNA included in this vector advantageously codes for a structure protein of a virus but it can also code for a regulatory protein.

The gene or complementary DNA carried by this vector can code for a least a portion of a hepatitis virus protein, in particular hepatitis B, and preferentially the protein HBs, in one of its forms S, S-preS2 or S-preS2-preS1, in which case the gene is gene S.

The virus may also be responsible for another hepatitis such as a hepatitis A or of a non-A, non-B hepatitis, such as a hepatitis C, E or delta.

The gene or protein sequences for these hepatitis viruses are described or may be deduced from the following documents:

patent FR-79 21 811, patent FR 80.09.039,
   patent EP-81.400.634, patent FR 84.03.564,
   patent EP 91.830.479 and the article by Najarian et al. (Proc. Natl. Acad. Sci. USA, 1985, 82, 2627-2631).

The vector may also include genes coding for at least a portion of the gp160 protein of HIV-1 virus associated with the p25 protein, and/or the p55 protein, and/or the p18 protein or at least a gene coding for the Rev protein of HIV-1 virus.

The vector may also include instead of a virus protein, a protein from a pathogenic micro-organism such as a protein from the bacterium causing diphtheria, whooping cough, listeriosis, the tetanus toxin etc.

The promoter carried by this vector is advantageously the promoter for the cytomegalovirus (CMV). It may however be any other promoter which allows the efficient expression of the gene in the muscle cells.

It may thus be:
   an internal or endogenic promoter, that is a promoter of the virus from which the gene is taken; such a promoter may be completed by a regulatory element of the muscle or another tissue, in particular an activating element,
   a promoter from a gene of a cytoskeleton protein, in particular desmine as described by BOLMONT et al. (Journal of submicroscopic cytology and pathology, 1990, 22, 117-122) et ZHENLIN et al. (Gene, 1989, 78, 243-254).
   the promoter from the virus HBV surface genes.

Generally, the promoter may be heterologous to the host, that is not naturally found in the host, but it is advantageously homologous, while being originally active in a tissue other than the muscle tissue.

In addition to the promoter, the vector may include a terminal transcription sequence, situated downstream of the gene.

Such vector may be the pCMV/HBS or pRCCMV-HBS plasmid, having the SEQ ID N° 1 sequence, filed under N° I-1370 with the Collection Nationale des Cultures des Micro-organismes de l'Institut Pasteur (CNCM) on 21 Oct. 1993.

It may also be the pRSV/HBS plasmid filed under N° I-1371 with the CNCM on 21 Oct. 1993.

This plasmid has a similar structure to pCMV/HBS but includes the Rous sarcoma virus (RSV) promoter instead of the cytomegalovirus (CMV) promoter.

Other plasmids may be:
   pCMVHB-S1.S2.S constructed by inserting the fragment Bgl II-Bgl II of the S gene, obtained from pCP10, into a pBlueScript vector modified to contain supplementary cloning sites in the "polylinker" portion. The fragment containing the S gene was then removed by KpnI-BssH II digestion then cloned into the corresponding sites of pcDNA 3 (In vitrogen, Rad Systems Europe Ltd, Abingdon UK) so as to obtain pCMVHB-S1.S2.S. This plasmid was filed under N° I-1411 with the CNCM.
   pCMVHB-S2.S obtained by eliminating the pre-S1 part of the HBS gene from pCMVHB-S1.S2.S by KpnI/MstI digestion, then by bonding the two extremities after treatment with S1 nuclease.
   pCMVHB-S2.S was filed with the CNCM under No. I-1410.
   pHBV-S1.S2.S, filed with the CNCM under N° I-1409, was obtained by inserting the S gene Bgl II-Bgl II fragment, obtained from pCP10, into a pBlueScript vector modified to contain supplementary cloning sites in the "polylinker" portion.

pBS-SKT-S1.S2.S codes for the three envelope proteins S, S-preS$_1$ and S-preS$_1$-preS$_2$ of the HBV virus.

The present invention further relates to nucleotide sequences comprising a promoter homologous to the host and another regulatory sequence for the expression of a gene or complementary DNA coding for one of the above mentioned proteins.

The present invention further relates to a vaccine or medicine containing at least one vector, or a nucleotide sequence, such as defined above.

It further relates to a composition capable of inducing a cytotoxic response comprised of at least one nucleotide sequence expressed in the muscle cells and including a promoter such as defined above.

It further relates to a non-lipid pharmaceutical composition for immunization against a viral infection such as a hepatitis including, on the one hand, at least a substance capable of inducing a coagulating necrosis of the muscle fibres and, on the other hand, a vector such as described above or including one of the nucleotide sequences, complete or partial, such as described above. By partial sequence is meant a sequence coding for at least 6 amino acids.

Said substance is advantageously bupivacaine.

Advantageously, said composition is characterized in that the vector is administered in the muscle of the individual to immunized, at least 5 days after the administration of the bupivacaine, and substantially in the same location.

Such prior administration of bupivacaine surprisingly allows to increase the effectiveness of the vector administration as well as the immunization of the individual.

Advantageously, the vector is administered ten days after administration of bupivacaine, and substantially in the same location of the individual's muscle.

The present composition may also contain additives which are compatible and pharmaceutically acceptable.

Such composition is preferentially administered by intramuscular injection. The injection can be carried out using a syringe designed for such use or using a liquid jet gun such as described by FURTH et al. (1992, Anal. Biochem. 205, 365-368).

The quantity of bupivacaine required to obtain sufficient degeneration of the muscle tissue, in order to achieve optimal immunization, is in the order of 0.10 mg to 10 mg per dose of injected composition.

The quantity of vector to be injected in order to achieve optimal immunization of the individual against a hepatitis varies according to the protein coded by the gene carried by the vector. As an indication, between 0.1 and 1000 µg of vectors are injected per individual.

The vectors may be obtained by methods known to those skilled in the art, in particular by synthesis or by genetic engineering methods.

Such methods are those described in particular in the technical manual:

Maniatis T. et al. 198213 Molecular Cloning, A Laboratory Manual, Cold Spring Harbour—Ed. New York.

The present invention is illustrated by, without in any way being limited to, the following examples, in which.

EXAMPLE 1

Induction of Antibodies Against a Hepatitis B Surface Antigen by Sequential Injection of Bupivacaine and of a Plasmid Carrying a Gene Coding for the Antigen 1) Materials and Methods 1.1 Bupivacaine Pretreatment All experiments were made on the muscles of the anterior tibia (AT) of mice C57BL/6J aged between 5 to 7 weeks.

A single degeneration-regeneration cycle of the muscle fibres is induced in the muscles of the anterior tibia of non-anaesthetized mice, by intramuscular injection of 50 µl marcaine (bupivacaine 0.5%, DMSO 1%) sold by Laboratoires Astra, France. The solution is injected using a tuberculosis syringe with a needle fitted into a polyethylene sleeve, in order to limit the penetration depth to 2 mm.

As marcaine is an anesthetic, injections into the right and left legs were performed at 10 to 30 minute intervals to prevent an overdose.

1.2 DNA Preparation

The plasmid used was constructed by cloning into a modified pBlueScript vector of the Xho I-Bgl II restriction fragment of the pCP10 plasmid which contains the gene coding for the HBS surface antigen and the non-translated sequences, both upstream and downstream, including the polyadenylation signal.

The S gene was then recovered by digestion using KpnI-BssHII enzymes and the fragment was cloned into the site of the pRC/CMV vector sold by In Vitrogen. The final plasmid construction was called pCMV-HBS and was filed under N° I-1370 with the CNCM.

Figure 1:
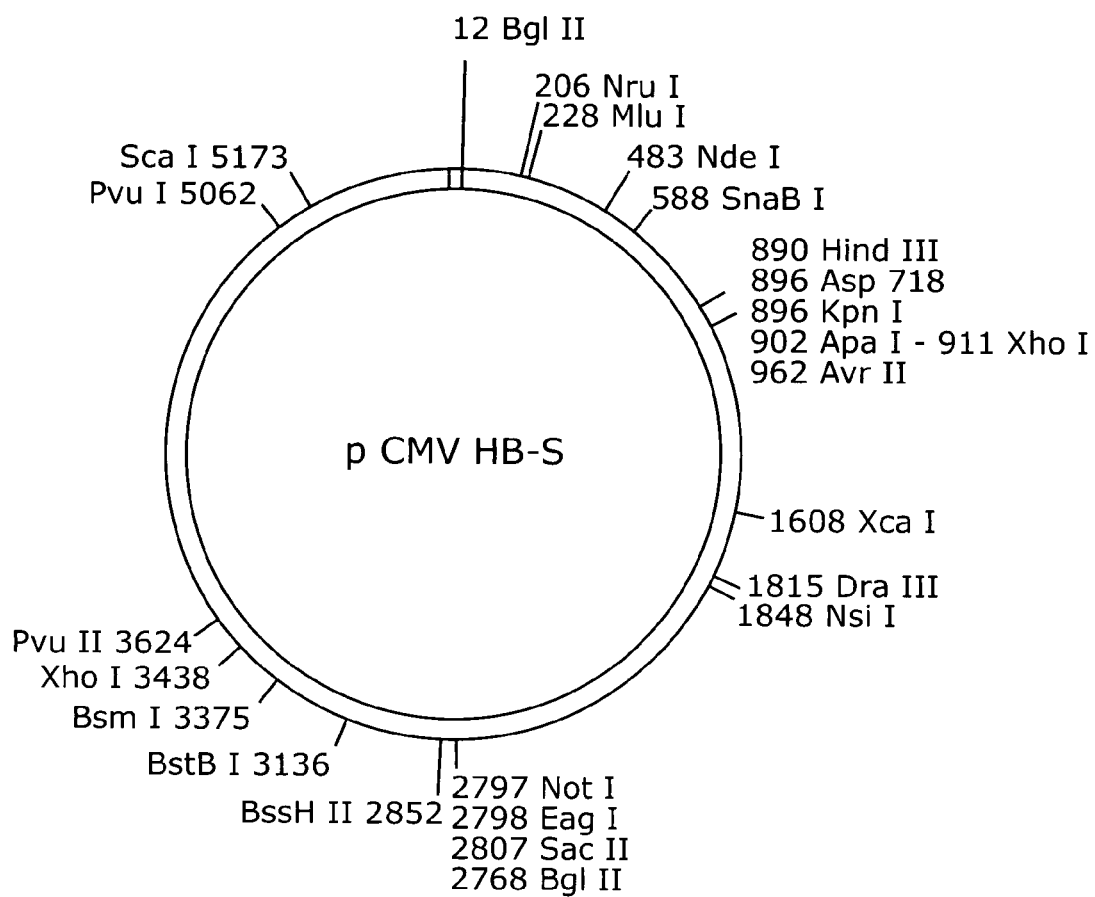
FIG. 1 is a schematic representation of pRC/CMV-HBs plasmid.

This plasmid is represented schematically in FIG. 1. The CMV promoter is situated between the 288 nucleotide which is the cleavage position of MluI and the 896 nucleotide, which is the cleavage position of KpnI. The DNA fragment including the structural gene of the HBs antigen structure was cloned between the 896 and 2852 nucleotides (position of BssH III).

The HBs gene spreads between the 911 (XhoI position) and 2768 nucleotides (Bgl II position) respectively.

The complete sequence for this plasmid is sequence SEQ ID N° 1.

The purified plasmid DNA was prepared by standard methods then redissolved in PBS buffer and stored at −20° C. until the injection was performed.

1.3 DNA Injection

One to five days after the marcaine injection, DNA was injected into the same area, the mouse being anaesthetized using sodium pentobarbital (75 mg/kg interperitonal path).

The DNA solution which contains 50 µg of plasmid DNA and 50 µl of PBS buffer was injected by a single intramuscular injection through the skin into the anterior tibia muscles undergoing regeneration.

The injections were performed bilaterally into the two legs of the mice, each animal thus receiving a total of 100 µg of recombinant plasmid DNA. As for the marcaine injection, the DNA solution was injected using the tuberculosis syringe with the needle described previously.

A single intramuscular DNA injection was performed in each leg.

2. Results

The results obtained are summarized in Table I below.

They show very clearly that a DNA injection after treatment with marcaine allows a large number of seric antibodies to be obtained against the hepatitis B surface antigen.

These results are surprising, from the analysis of the state of the art it was not inferred that a plasmid would allow the induction of anti-HBs antibodies which could be found in the serum and thus allow an effective vaccination.

The ease of application of the plasmid vaccination, and the fact that boosters would not be necessary, allows the consideration of a large scale vaccination.

EXAMPLE 2

Comparison of the Efficiency of a Plasmid Injection in the Presence and Absence of Lipids.

A dose of 10 µg plasmid DNA from the SV40-luciferase vector available commercially ("pGL2-Control Vector" from Promega, reference E1 11) in 50 µl of physiological solution was injected into the sucrose pretreated muscle following the method of David et al. (Hum. Gene Ther. 4:151-159 (1993)). The injected DNA is mixed earlier with lipids such as dioctadecylamidoglycyl spermine (DOGS) or the following mixtures: DOGS+spermidine, and DOGS+polyethyleneglycol (PEG). The luciferase activity was determined 5 days after the injection.

These results are shown in table II below.

They show that the presence of lipids (DOGS) very reduces significantly the efficiency of the plasmid injection with respect to a composition with no lipids (control).

EXAMPLE 3

Comparison of the Responses of Mice and Rabbits to Plasmids Carrying Different Promoters and Envelope Genes for the HBV Virus.

Figure 2A:
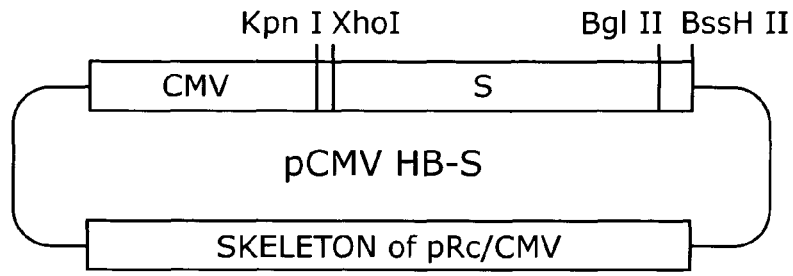
FIGS. 2A to 2D are schematic representations of pCMVHB-S, pCMVHB-S2.S., pCMVHB-S1.S2.S and pHBV-S1.S2.S plasmids, respectively.
Figure 2B:
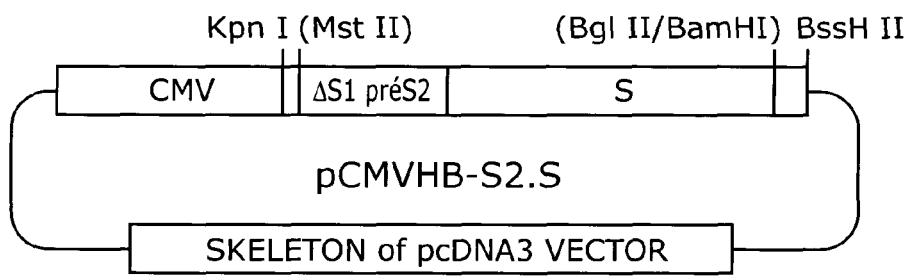
Figure 2C:
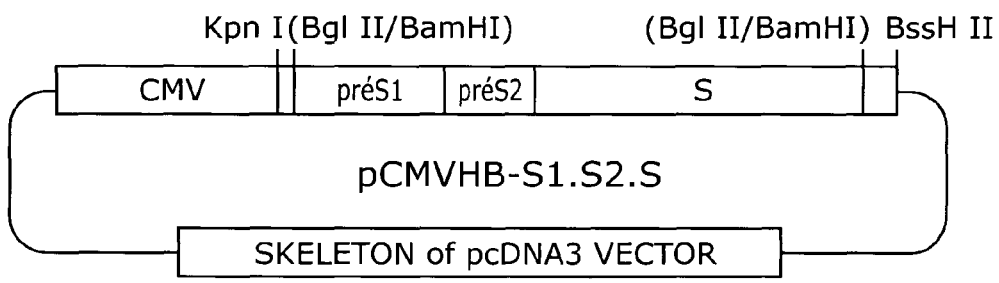
Figure 2D:
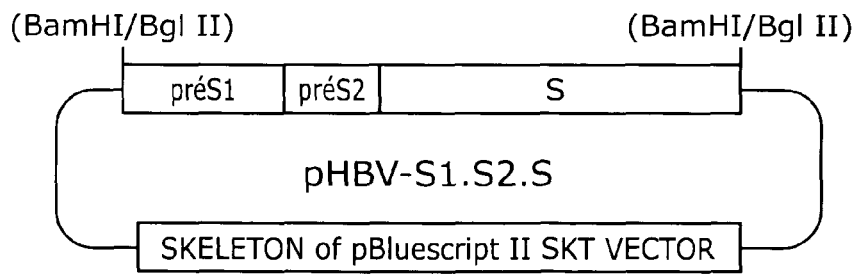
Figure 3:
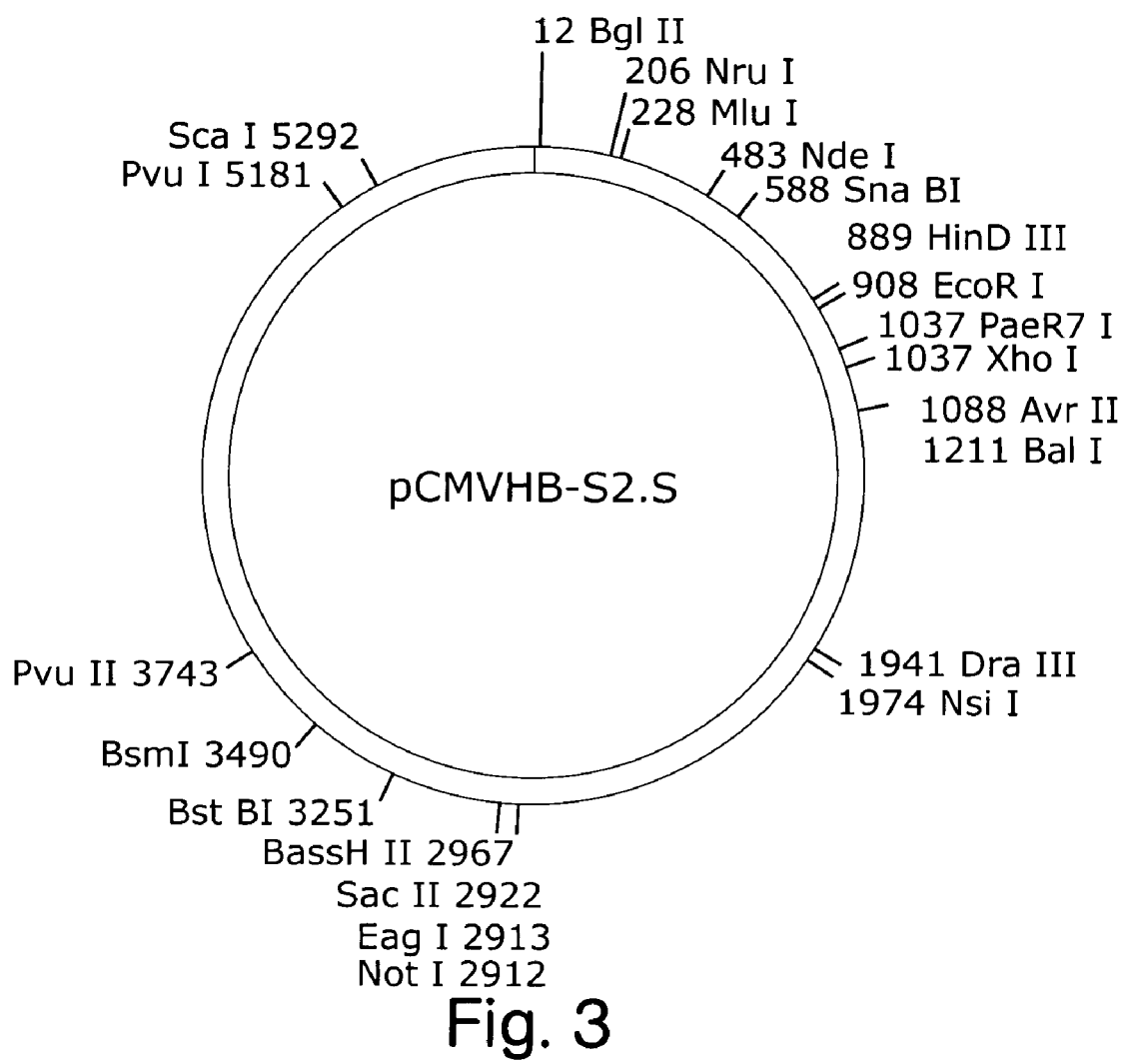
FIGS. 3, 4 and 5 are schematic restriction maps for pCMVHB-S2.S, pCMVHB-S1.S2.S and pRSV-HBS plasmids, respectively.
Figure 4:
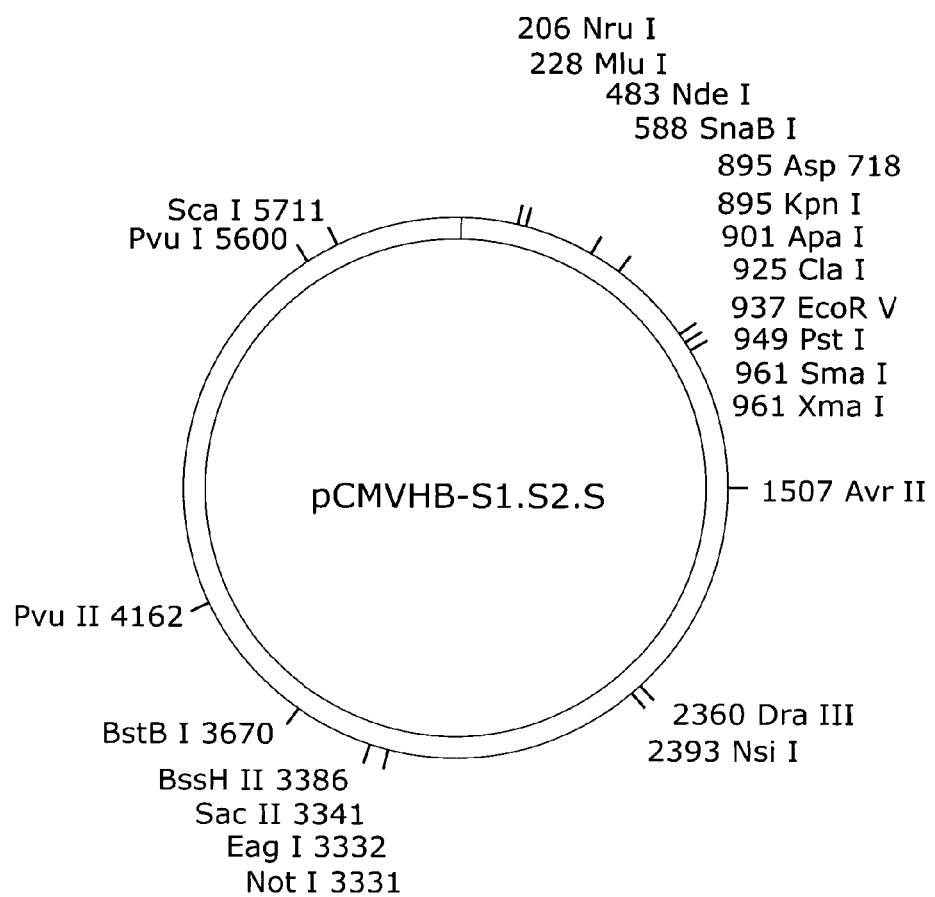
Figure 5:
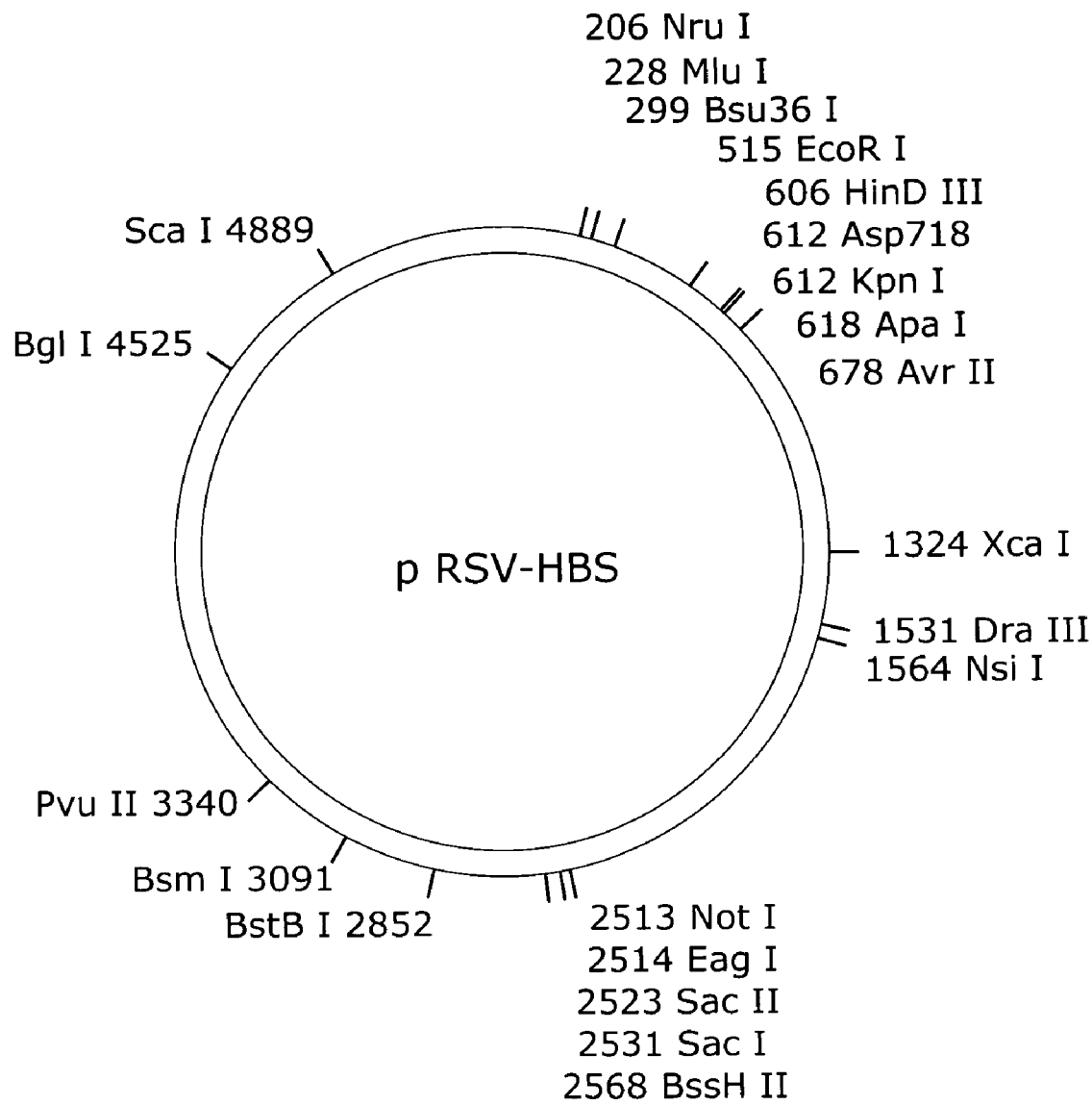

Four plasmids were constructed allowing the expression of one, two or three envelope proteins for the HBV virus. In three of the constructions (pCMVBH-S, pCMVHB-S2.S, pCMVHB-S1.S2.S) the genes coding for the HBV virus envelope proteins are put under transcriptional control of the promoter of the CMV virus precursor genes (FIG. 1, FIG. 2A to 2C, FIGS. 3 and 4). The fourth plasmid (pHBV-S1.S2.S) uses the promoter for the HBV virus surface genes contained in the pre-S1 region of this virus (Cattaneo et al. (1983) Nature, 305, 336) (FIG. 2D) as a transcriptional controlling element. In the four constructions, the polyadenylation signal used is contained in the HBV sequences present in 3' of the S gene.

1. In Vitro Control of the Vector Efficiency.

Figure 6:
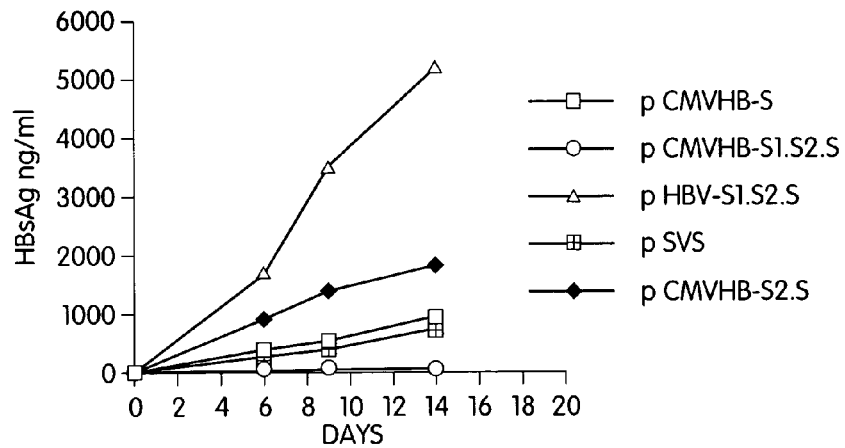
FIG. 6 illustrates the secretion of antigenic HBs particles (HBs Ag) in ng/ml (ordinates) as a function of the number of days (abscissa) for cells carrying the pCMVHB-S, pCMVHB-S1.S2.S, pHBV-S1.S2.S, pSVS or pCMVHB-S2.S plasmids.

To control the efficiency of these vectors in vitro in eucaryote cells, mouse fibroblasts or myoblasts were transfected. A plasmid expressing the three envelope proteins under control of the SV40 promoter (pSVS) was used as a control (Michel et al. 1984, Proc. Natl. Acad. Sci. USA, 81, 7708-7712)). FIG. 6 illustrates the secretion kinetics of the HEs particles in the culture supernatants. The low antigen levels produced by transfection of the pCMVHB-S1.S2.S vector are compatible with a large degree of synthesis of the large envelope protein starting from the CMV promoter. This protein being myristilised in its amino terminal region, is retained in the endoplasmic reticulum (Ganem, (1991), Current Topics in Microbiology and Immunology, 168, 61-83). Retention in the cell of proteins carrying the pre-S1 determinants was confirmed by immunofluorescence.

Figure 7A:
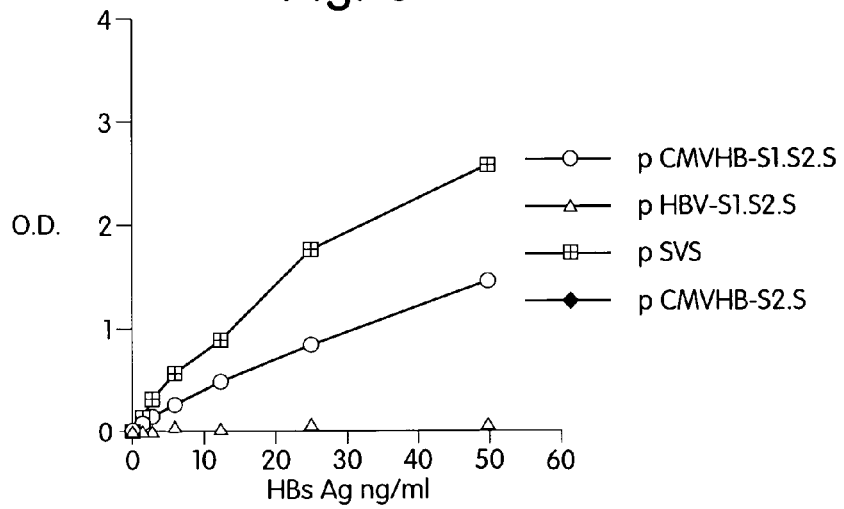
FIGS. 7A and 7B illustrate the determination on some particles in FIG. 6 of the presence of the preS$_1$ and PreS$_2$ antigens using respectively anti-preS$_1$ and anti-preS$_2$ antibodies. The formation of antibody-antigen complexes is shown by the optical density (ordinates), as a function of antigen concentration.
Figure 7B:
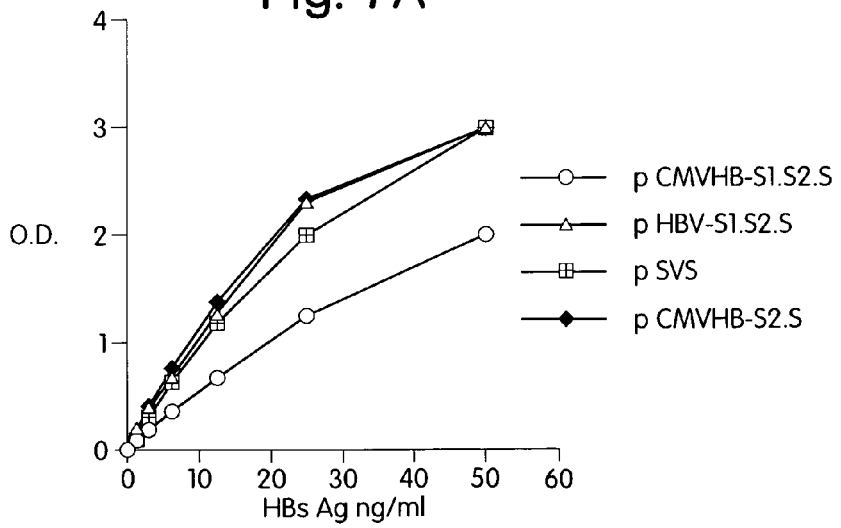
Figure 8A:
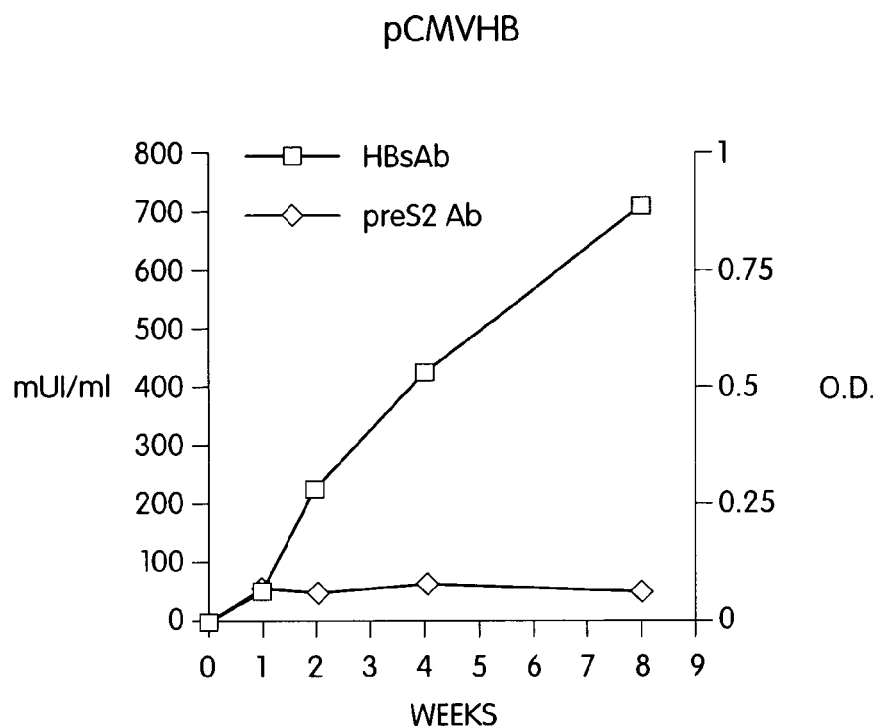
FIGS. 8A to 8D represent the anti-HBS responses (HBS Ab as ordinate, expressed as mUI/ml) and anti-preS2 (preS2 Ab as ordinate, expressed in O.D.) of mice vaccinated by pCMVHB-S (8A), pCMVHB-S2.S (8B), pCMVHB-S1.S2.S (8C) and pHBV-S1.S2.S (8D), respectively.
Figure 8B:
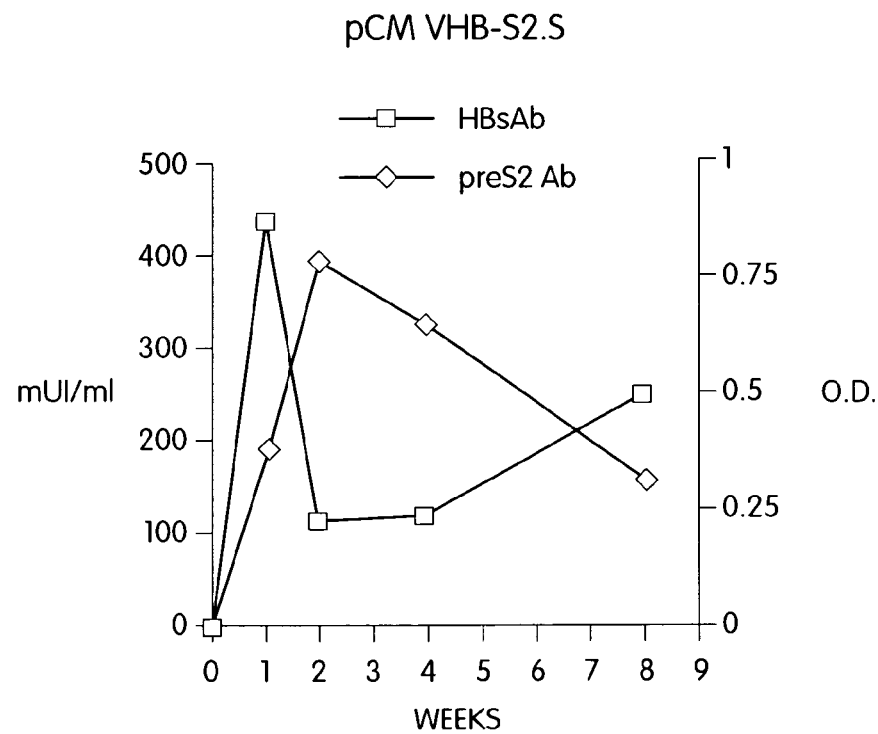
Figure 8C:
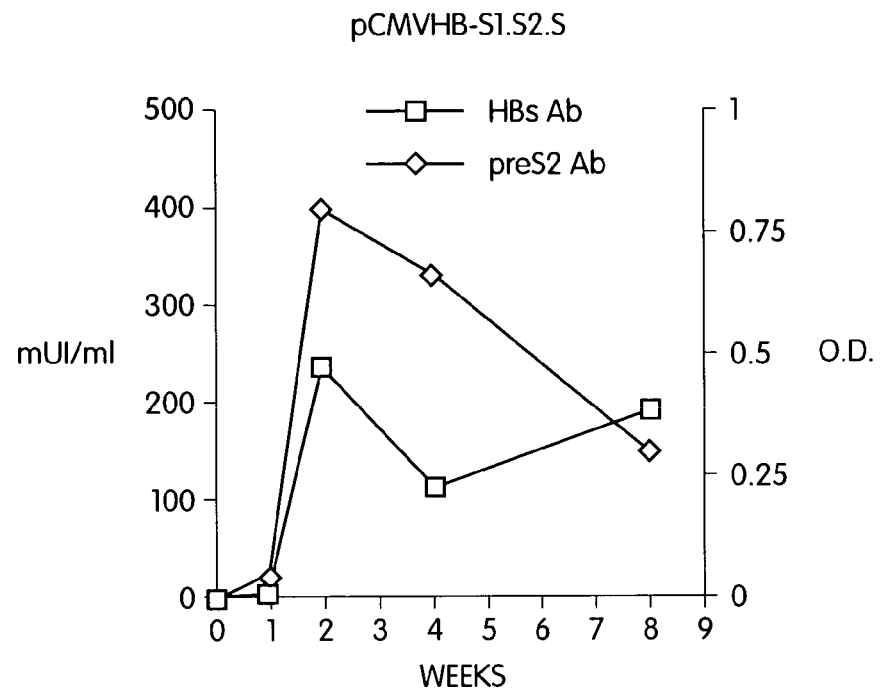
Figure 8D:
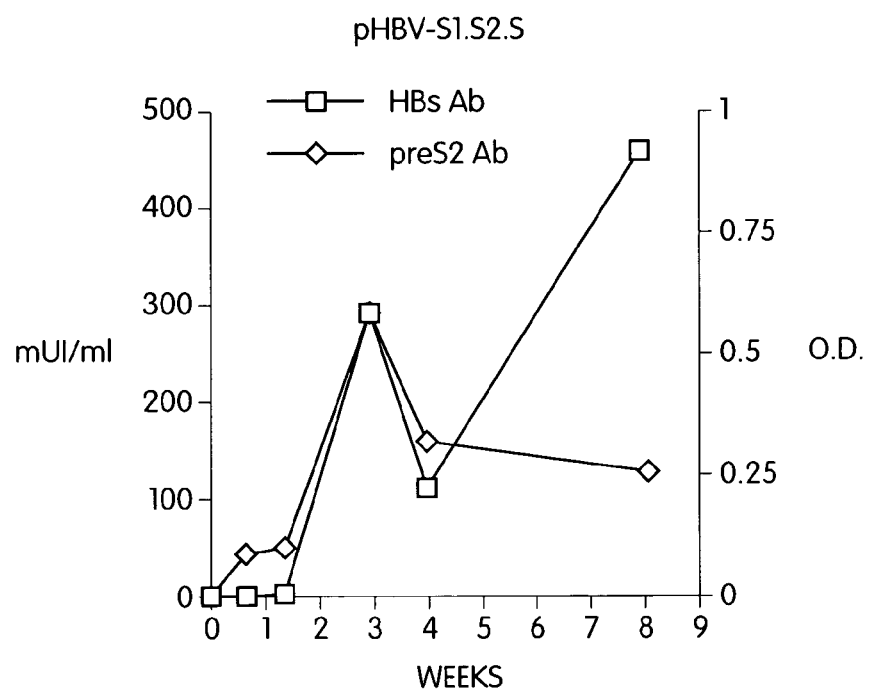

The composition of the secreted particles was analyzed in an ELISA sandwich system using as capture antibodies a monoclonal mouse antibody specific to the pre-S1 (FIG. 7A) or pre-S2 (FIG. 7B) determinants as capture antibodies and rabbit anti-HBs polyclonal serum as second antibodies. These experiments show that the AgHBs particles produced starting from pCMVHB-S1.S2.S vector carry pre-S1 and Pre-S2 determinants showing the presence of the large and medium envelope proteins of the HBV virus. Particles secreted after the transfection of the pCMVHB-S2.S and pHBV-S1.S2.S vectors carry, in addition to the HBs determinants, pre-S2 determinants characteristic of the medium envelope proteins.

2) DNA Inoculation

DNA purified on a Quiagen column was injected by an intramuscular path in a single injection of 100 µg (50 µg/leg) in the anterior tibia muscle of mice C57/BL6 (8 mice per group). Five days prior to the injection, the muscle was pretreated with cardiotoxin in order to induce degeneration followed by regeneration of the muscles cells thus favoring the DNA capture by these cells.

The DNA injection experiments were also carried out for rabbits. In this case, pCMVHB-S DNA was administered into normal muscle without degeneration, either by using an injection gun without needle called Biojector$^R$, or by conventional syringes fitted with needles.

3) Anti-Hbs Responses for Mice Vaccinated with DNA

An anti-HBs antibody response is induced by a single injection of one or other of the four plasmids used.

The antibody response was analyzed using a commercial anti-HBs antibodies detection kit (Monolisa anti-HBs, Diagnostic Pasteur). Anti-preS2 antibodies are detected by an ELISA system using, on the solid phase, a peptide from the pre-S2 (AA 120-145) region on the solid phase corresponding to a B major epitope carried by this area (Neuarth et al., (1985), Nature, 315, 154).

FIGS. 8A to 8D illustrate the anti-HBs (HBs-Ab) response kinetics expressed in milli-international units/ml and the anti-pre-S2 response (pres2Ab) determined as optical density (492 nm) for 1/100 diluted serums. Detection was carried out using a mouse anti-immunoglobulin antibody (IgG) coded with peroxidase.

The injection of the pCMVHB-S plasmid (FIG. 8A) induces a constant anti-HBs antibody synthesis. Seroconversion was observed in 100% of mice from one week after the injection with an antibody average level of 48 mUI/ml (from 12 to 84 mUI/ml, standard deviation (SD)=28), which is 4 to 5 times superior to the threshold required in man to provide protection (10 mUI/ml).

The induced response for a single injection of pCMVHB-S2.S plasmid (FIG. 8B) is characterized by the very early apparition of anti-HBs antibodies. These antibodies reach an average level of 439 mUI/ml (from 104 to 835 mUI/ml; SD=227) at one week then reduce before increasing again to reach the initial level at 13 weeks. The significance of this antibody peak will be discussed later. A peak for anti-pre-S2 IgG antibodies is observed at two weeks.

The appearance of anti-HBs antibodies induced by injection of pCMVHBV-S1.S2.S plasmids. (FIG. 8C) and pHBV-S1.S2.S (FIG. 8D) is slightly delayed as the mice only seroconvert to 100% after two weeks. The seroconversion profile is identical, it is characterized by an initial response which is specific to the pre-S2 antigen followed by an anti-HBs response which gradually increases to reach a level of 488 mUI/ml (from 91 to 1034 mUI/ml; SD=552) (pCMVHB-S1.S2.S) and 1725 mUI/ml (from 143 to 6037 mUI/ml; SD=1808) (pHBV-S1.S2.S) at 13 weeks.

4) Anti-HBS Response of Rabbits Injected with DNA

Results presented in tables III and IV show that the antibody levels detected at 8 weeks in rabbits immunized using the Biojector are significantly higher than those obtained by a DNA injection by needle.

5) Qualitative Analysis of the Humoral Response

ELISA systems applied to the solid phase of the HBs antigens of varying composition with respect to the determinants presented on the solid phase and using mouse antibodies specific to IgM or IgG as second antibodies gave a qualitative analysis of the antibody response that was achieved.

In all cases, the single injection of DNA in mice is characterized by the early appearance of AgHBs specific IgM followed immediately by conversion to IgG isotype antibodies which is characteristic of the memory response induced by the auxiliary T cells. The antibody response to the DNA injection is characterized by its prematurity. Indeed, seroconversion is achieved 8 to 15 days after the injection depending on the DNA type used and in all cases the plateau is achieved in four weeks and maintained constantly over a period of 12 weeks.

The use of the heterologous sub-type HBs antigens (ad) fixed on ELISA plates allows the formation/detection of the presence, in the serum of immunized mice, of antibodies specific to the anti-a group, and by difference in reactivity with respect to AgHBs of the same sub-type (ay), of antibodies specific to the anti-y sub-type. The presence of antibodies specific to determinants of the AgHBs group is very important as the former are capable of giving protection against the heterologous sub-type virus during virulent tests in chimpanzees (Szmuness et al. (1982) N. Engl. J. Med. 307, 1481-1486)

Figure 9:
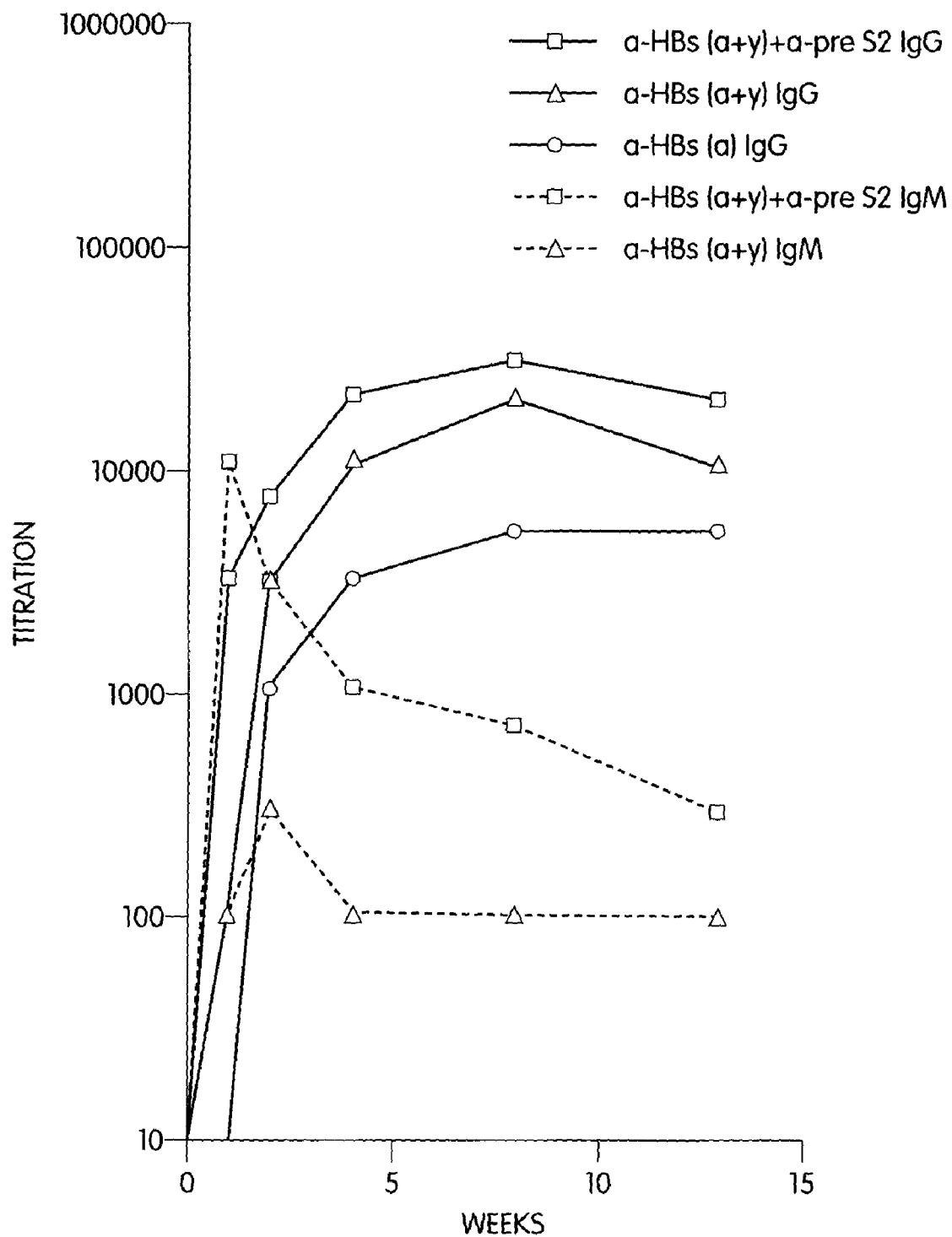
FIG. 9 illustrates the antibody response, IgG and IgM immunoglobulins (titre as ordinates), of a mouse vaccinated by pCMVHB-S2.S as a function of the number of weeks (abscissa).
Figure 10A:
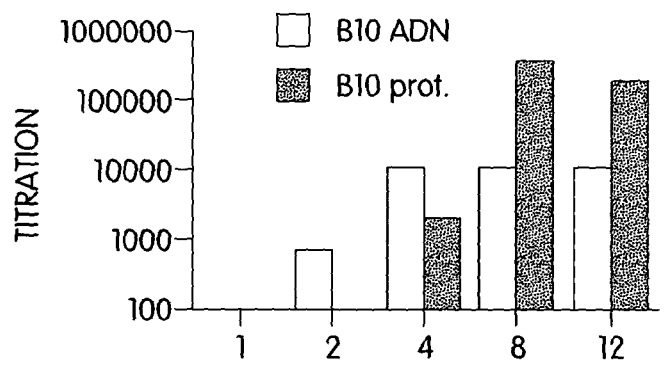
FIGS. 10A to 10C represent the anti-group and anti-subtype ay responses induced by DNA from pCMV-S (DNA) or from the HBS antigen (prot), respectively in mice B10 (10A), BIOS (10B) and B10M (10C).
Figure 10B:
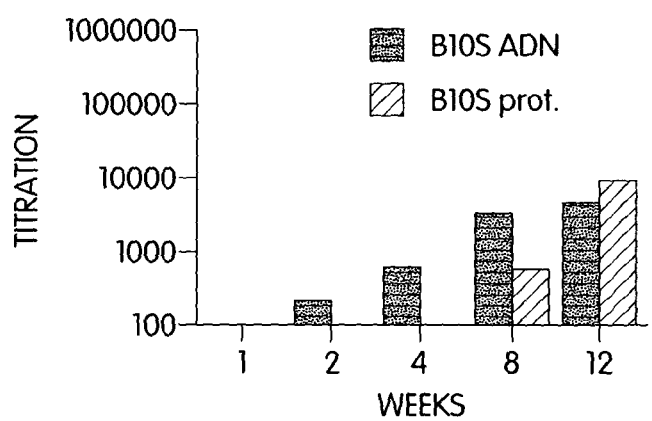
Figure 10C:
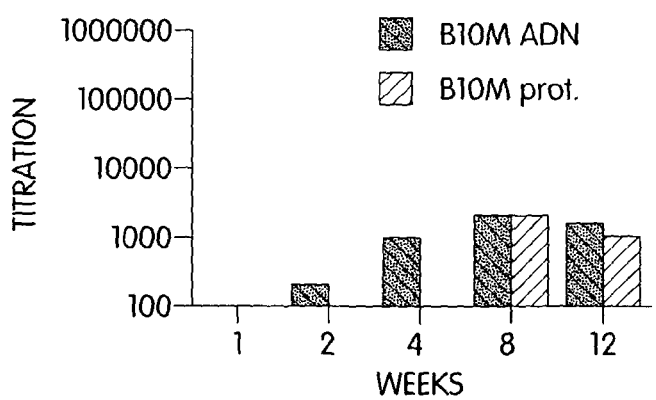
Figure 10D:
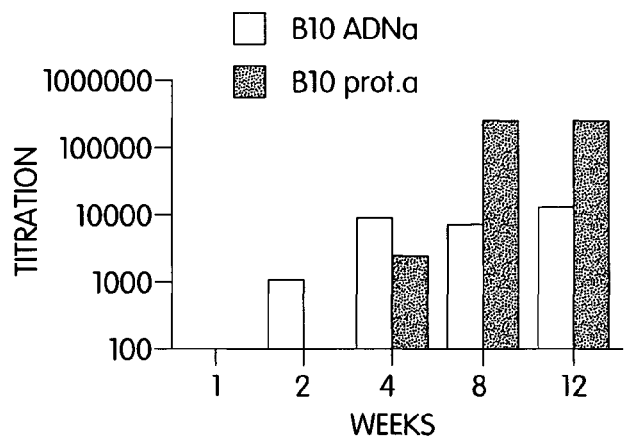
FIGS. 10D to 10F represent the antigroup responses induced by DNA from pCMV-S (DNA) or from the HBS antigens (prot), respectively in mice B10 (10D), B10S (10E) and B10M (10F).
Figure 10E:
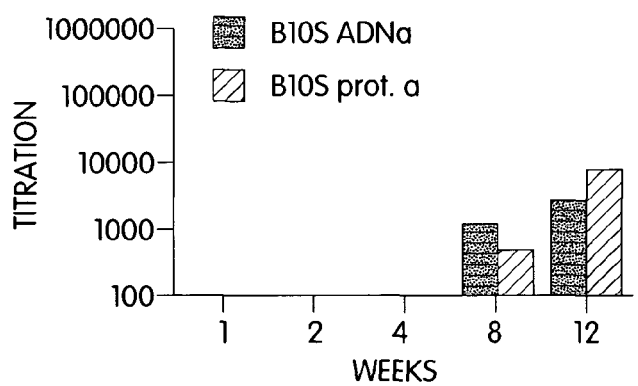
Figure 10F:
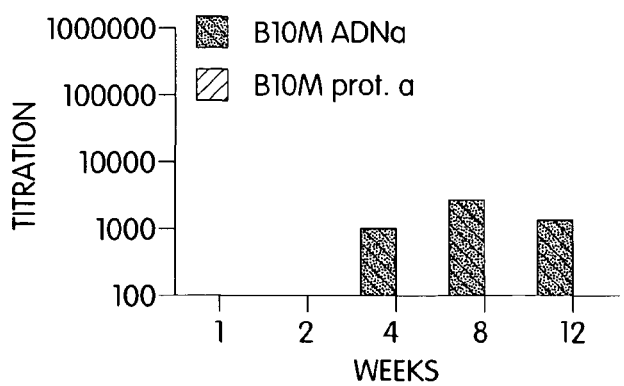
Figure 11:
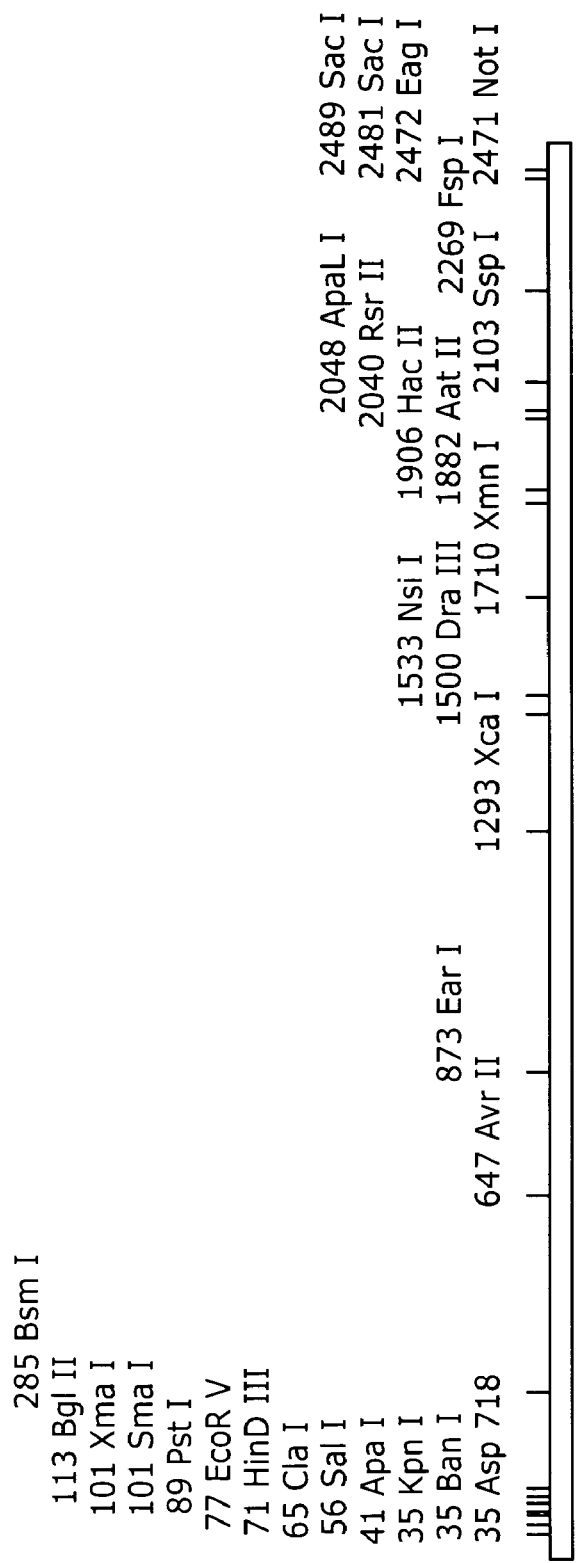
FIG. 11 represents a linear restriction map for the pBS-SKT-S1.S2.S plasmid.

Analysis of the response induced by the pCMV-S2.S vector shows that it has a remarkable similarity with the one which can be observed in man during infection. It is characterized by an extremely early (8 days) peak for IgM which is specific to the pre-S2 region immediately followed by conversion to anti-pre-S2 IgG (FIG. 9). This response is followed by the appearance of IgM then IgG anti-HBs antibodies. The anti-HBs antibody production is constant and reaches a maximum after 4 weeks. At 13 weeks IgG anti-HBS and anti-pre-S2 remain at a constant level.

The anti-sub-group (y) response precedes that of the anti-group response (a) in the same way as that described for the vaccination with the recombinant vaccine (Tron et al., (J. Infect. Dis. 160, 199-204).

The response obtained with the three other DNA vaccines illustrates the commutation of class IgM→IgG which is characteristic of the secondary response. The response being first of all directed against the sub-type before being against the AgHBs group determinants.

The long term response which was studied for pCMVHB-S DNA shows that the antibody peak is reached within 3 months and this remains at a constant level 6 months later (Table V).

6. Genetic Vaccine and Non-response

The high number of non-responders to the classical vaccine (2.5 to 5) remains a major problem for vaccination against hepatitis B. It has been possible to correlate the non-response in man to certain HLA types (Krustall et al., (1992) J. Exp. Med. 175, 495-502) and to a defect in the antigen presentation or stimulation of the auxiliary T cells.

To study the possible impact of the genetic vaccination on the AgHBs non-response, a range of mice strains were used for which the response to various HBV virus envelope proteins is controlled genetically and has been well characterized by Millich et al. (1986 J. Immunol. 137, 315). The pCMVHB-S construction previously described was injected into B10 ($H-2^b$) B10.S ($H-2^s$) and B10.M ($H-2^f$) mice muscles.

The B10 strain responds to the three virus envelope proteins, the B10.S strain does not respond to AgHBs but this non-response can be overcome by immunization with HBsAg antigens which are carrying pre-S2 determinants. The B10M strain is totally non-responsive to both HBs and pre-S2 antigens. A response for the latter strain can be achieved by immunization using AgHBs carrying pre-S1 determinants.

The mice immunized by the DNA received a single injection (100 μg) in the regenerating muscle. Control mice were injected with two intraperitonal injections of protein at an interval of one month, the first of 2 μg AgHBs to which the complete Freund additive (CFA) was added and the second of 2 μg AgHBs to which the incomplete Freund additive (IFA) was added.

The results obtained for pCMVHB-S are illustrated by FIGS. 10A to 10F.

In the B10 strain (good responder) the DNA induced response is earlier than that induced by the protein after a single injection.

The appearance of anti-HBs antibodies sub-type specific then group specific after immunization with pCMVHB-S DNA was observed in the B10S strain (non-responder to AgHBS in the absence of pre-S2). Group specific anti-HBs antibodies are observed in HBs protein immunized mice only after the second injection.

A group and sub-type specific anti-HBs response is obtained for DNA immunization of strain B10M (non-responder to AgHBs in absence of pre-S1) whereas only a sub-type specific response is induced by the protein with two injections being required.

The response induced by the three vector types is compared in the three mice strains.

CONCLUSIONS

It is generally thought that the humoral response to HBs antigens is sufficient by itself to give protection. The presence of antibodies directed against other determinants (pre-S1 and pre-S2) carried by the virus envelope proteins, themselves protectors, could improve the response quality. The experiments reported here as a whole illustrates that the humoral response induced by the genetic anti-hepatitis B vaccination is greater in several fields than that which can be achieved for the classical vaccination.

In terms of seroconversion levels: the 100% level is obtained, after only one injection, from day 8 for mice immunized with pCMV-HBS DNA and pCMVHB-S2.S.

In terms of response level: the 10 mUI/ml threshold level, considered sufficient to give protection in man, is always greatly exceeded.

In terms of the speed of response: in 8 days a very high level of anti-pre-S2 antibodies is obtained for the pCMVHB-S2.S vector and it is known that the former are capable of giving protection by themselves (Itoh et al., (1986) Proc. Natl. Acad. Sci. USA 83, 9174-9178).

In terms of response stability: anti-HBs anti-bodies remain constant at a high level for more than 6 months.

In terms of response quality: type IgG antibodies characteristic of a response which is dependent on the auxiliary T cells and therefore on a memory response are obtained.

In terms of anti-viral activity: the antibodies are specific to the viral sub-type but especially group specific and therefore susceptible to giving a cross protection.

In terms of biological significance: the response profile obtained by pCMVHB-S2.S immunization mimes totally that which is observed in man after a resolved viral infection.

Deposits: Nucleotide plasmid vectors pCMV/HBS, pRSV/HBS, and pCMV/HB-S 1.S2.S, pHBV-S1.S2.S, and pCMVHB-S2.S were deposited on Oct. 21, 1993 with the Collection Nationale des Cultures des Micro-organismes de l'Institut Pasteur (CNCM) under accession numbers I-1370, I-1371, I-1411,I-1409, and I-1410, respectively. Applicants' assignee, the University of Ottawa, represents that the CNCM is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 C.F.R. §1.14 and 35 U.S.C. §122. The deposited material will be maintained with all the care necessary to keep it viable and uncontaminated for a period of at least five years after the most recent request for the furnishing of a sample of the deposited vector, and in any case, for a period of at least thirty (30) years after the date of deposit or for the enforceable life of the patent, whichever period is longer. Applicants acknowledge their duty to replace the deposit should the depository be unable to furnish a sample when requested due to the condition of the deposit.

TABLE I

Induction of antibodies against the hepatitis B surface antigen

| | | Level of antibodies against hepatitis B surface antigen in the serum (mIU/ml) | | |
| --- | --- | --- | --- | --- |
| Description | Number of mice | Before DNA injection | 15 days after DNA injection | 35 days after DNA injection |
| DNA injected 1 day after marcaine treatment | 5 | 0 | average: 56 from 5 to > 140 | average: 59 |

TABLE I-continued

Induction of antibodies against the hepatitis B surface antigen

| Description | Number of mice | Before DNA injection | Level of antibodies against hepatitis B surface antigen in the serum (mIU/ml) | |
|---|---|---|---|---|
| | | | 15 days after DNA injection | 35 days after DNA injection |
| DNA injected 5 days after marcaine treatment | 5 | 0 | average: 71 from 21 to >108 | average: 47 |

TABLE II

| Group | Luciferase RLU/sec/muscle (Average ± SEM) RLU = Relative Light Unit | Percentage relative to the control |
|---|---|---|
| Control | 43 082 ± 5 419 | 100% |
| 4X DOGS | 28 ± 7 | 0.06% |
| DOGS - Spermidine | 50 ± 23 | 0.12% |
| PEG-DOGS | 0 ± 0 | 0.00% |

TABLE III

Immunization with the Biojector$^R$

| pCMV-HB.S N° | 0 weeks | 2 weeks | 8 weeks |
|---|---|---|---|
| 2.1 | 0 | 517 | 380 |
| 2.2 | 0 | 374 | 322 |
| 3.1 | 0 | 258 | 418 |
| 4.1 | 0 | 400 | 4045 |
| 4.2 | 0 | 88 | 86 |
| 4.3 | 0 | 314 | 420 |
| 6.1 | 0 | 415 | 1001 |
| 6.2 | 0 | 1543 | 3517 |
| 6.3 | 0 | 1181 | 141 |
| Average | 0 | 566 mUI/ml | 1148 mUI/ml |
| SD | 0 | 476 | 1521 |
| SEM | 0 | 159 | 507 |
| N | 9 | 9 | 9 |
| CV | | 84% | 133% |

TABLE IV

Immunization by injection using a needle

| pCMV-HB.S N° | 0 weeks | 2 weeks | 8 weeks |
|---|---|---|---|
| 1.1 | 1 | 0 | 1 |
| 5.1 | 0 | 287 | 186 |
| 5.2 | 0 | 162 | 798 |
| 5.3 | 0 | 305 | 203 |
| 7.1 | 0 | 86 | 175 |
| 7.2 | 0 | 1108 | dead |
| Average | 0 | 325 mUI/ml | 273 mUI/ml |
| SD | 0 | 401 | 305 |
| SEM | 0 | 164 | 136 |
| N | 6 | 6 | 5 |
| CV | 245% | 124% | 112% |

TABLE V

Long term response of a mouse vaccinated with pCMVHB-S

| | 1 month | 2 months | 3 months | 6 months |
|---|---|---|---|---|
| * a-HBs titre in mUI/ml | 227 | 662 | 1299 | 1082 |
| * a-HBs ELISA titre | $3.5 \times 10^{-4}$ | $5 \times 10^{-4}$ | $8.5 \times 10^{-4}$ | $9 \times 10^{-4}$ |

---

The invention claimed is:

1. A method of inducing an antigen specific immune response in a mammalian subject comprising
administering to the mammalian subject an expression plasmid vector that comprises a gene encoding a hepatitis B virus surface or core antigen, or a fragment thereof, and a promoter for expression of the gene in the subject, wherein the gene is expressed in the mammalian subject in an effective amount to induce an antigen specific immune response against the hepatitis B virus surface or core antigen.

2. The method of claim 1, wherein administration of said vector is conducted at least five days after administration of at least one substance capable of inducing a coagulating necrosis of muscle fibers and wherein said administration of said vector and said substance is about in the same area.

3. The method of claim 2, wherein said substance is bupivacaine.

4. The method of claim 3, wherein the vector is administered at least 7 days after the administration of bupivacaine.

5. The method of claim 1, wherein the administration is carried out by intramuscular injection.

6. The method according to claim 5, wherein the intramuscular injection is carried out using a liquid jet gun.

7. The method of claim 1, wherein the promoter is endogenous to hepatitis B virus.

8. The method of claim 1, wherein the antigen is a protein or antigenic portion thereof selected from the group consisting of major/small envelope protein (S), middle envelope protein ($S_2$-S), and large envelope protein ($S_1$-$S_2$-S).

9. The method of claim 8, wherein the gene encodes the S protein.

10. The method of claim 1, wherein the promoter is a viral promoter.

11. The method of claim 10, wherein the promoter is a cytomegalovirus promoter.

12. The method of claim 1, wherein the promoter is a mammalian promoter.

13. The method of claim 1, wherein the vector is pCMV-HB-S1.S.S deposited with the CNCM under No. I-1411.

14. The method of claim 1, wherein the vector is pCMV-HB-S2.S deposited with the CNCM under No. I-1410.

15. The method of claim 1, wherein the vector is pRSV-HBS deposited with the CNCM under No. I-1371.

16. The method of claim 1, wherein the vector is pHBV-S1.S2.S deposited with the CNCM under No. I-1409.

* * * * *

SEQUENCE LISTING

```
<160> NUMBER OF SEQ ID NOS: 1

<210> SEQ ID NO 1
<211> LENGTH: 5618
<212> TYPE: DNA
<213> ORGANISM: Unknown
<220> FEATURE:
<223> OTHER INFORMATION: Oligonucleotide vector
<300> PUBLICATION INFORMATION:
<302> TITLE: Nucleotide vector, composition containing such vector and
      vaccine for immunization against hepatitis
<308> DATABASE ACCESSION NUMBER: A4471 GenBank, EMBL, DDBJ
<309> DATABASE ENTRY DATE: 1997-03-07
<310> PATENT DOCUMENT NUMBER: WO9511307
<312> PUBLICATION DATE: 1995-03-27

<400> SEQUENCE: 1
gacggatcgg gagatctccc gatcccctat ggtcgactct cagtacaatc tgctctgatg        60
ccgcatagtt aagccagtat ctgctccctg cttgtgtgtt ggaggtcgct gagtagtgcg       120
```

-continued

```
cgagcaaaat ttaagctaca acaaggcaag gcttgaccga caattgcatg aagaatctgc      180
ttagggttag gcgttttgcg ctgcttcgcg atgtacgggc agatatacg cgttgacatt       240 gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggac tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acgtgggag gtctatataa gcagagctct ctggctaact agagaaccca       840
ctgcttaact ggcttatcga aattaatacg actcactata gggagaccca gcttggtac       900 cgggccccc ctcgaggatt ggggaccctg cgctgaacat ggagaacatc acatcaggat       960
tcctaggacc ccttctcgtg ttacaggcgg ggttttttctt gttgacaaga atcctcacaa     1020
taccgcagag tctagactcg tggtggactt ctctcaattt tctaggggga actaccgtgt      1080
gtcttggcca aaattcgcag tccccaacct ccaatcactc accaacctct tgtcctccaa      1140
cttgtcctgg ttatcgctgg atgtgtctgc ggcgttttat catcttcctc ttcatcctgc      1200
tgctatgcct catcttcttg ttggttcttc tggactatca aggtatgttg cccgtttgtc      1260
ctctaattcc aggatcctca acaaccagca cgggaccatg ccggacctgc atgactactg      1320
ctcaaggaac ctctatgtat ccctcctgtt gctgtaccaa accttcggac ggaaattgca      1380
cctgtattcc catcccatca tcctgggctt tcggaaaatt cctatgggag tgggcctcag     1440
cccgtttctc ctggctcagt ttactagtgc catttgttca gtggttcgta gggctttccc      1500
ccactgtttg gctttcagtt atatggatga tgtggtattg ggggccaagt ctgtacagca      1560
tcttgagtcc ctttttaccg ctgttaccaa ttttctttg tctttgggta tacatttaaa       1620
ccctaacaaa acaaagagat gggttactc tctaaatttt atgggttatg tcattggatg       1680
ttatgggtcc ttgccacaag aacacatcat acaaaaaatc aaagaatgtt ttagaaaact      1740
tcctattaac aggcctattg attggaaagt atgtcaacga attgtgggtc ttttgggttt      1800
tgctgcccct tttacacaat gtggttatcc tgcgttgatg cctttgtatg catgtattca      1860
atctaagcag gctttcactt tctcgccaac ttacaaggcc tttctgtgta acaataccct      1920 gaaccttttac cccgttgccc ggcaacggcc aggtctgtgc caagtgtttg ctgacgcaac     1980
ccccactggc tggggcttgg tcatgggcca tcagcgcatg cgtggaacct tttcggctcc      2040
tctgccgatc catactgcgg aactcctagc cgcttgtttt gctcgcagca ggtctggagc      2100
aaacattatc gggactgata actctgttgt cctatcccgc aaatatacat cgtttccatg      2160
gctgctaggc tgtgctgcca actggatcct gcgcgggacg tccttttgttt acgtcccgtc     2220 ggcgctgaat cctgcggacg acccttctcg gggtcgcttg ggactctctc gtccccttct     2280
ccgtctgccg ttccgaccga ccacggggcg cacctctctt tacgcggact ccccgtctgt     2340
gccttctcat ctgccggacc gtgtgcactt cgcttcacct ctgcacgtcg catggagacc     2400
accgtgaacg cccaccaaat attgcccaag gtcttacata agaggactct tggactctca    2460
gcaatgtcaa cgaccgacct tgaggcatac ttcaaagact gtttgtttaa agactgggag    2520
```

-continued

```
gagttggggg aggagattag gttaaaggtc tttgtactag gaggctgtag gcataaattg      2580
gtctgcgcac cagcaccatg caactttttc acctctgcct aatcatctct tgttcatgtc      2640
ctactgttca agcctccaag ctgtgccttg ggtggctttg gggcatggac atcgacccct      2700
ataaagaatt tggagctact gtggagttac tctcgttttt gccttctgac ttctttcctt      2760
cagtacgaga tctggccagg atccactagt tctagagcgg ccgccaccgc ggtggagctc      2820
cagcttttgt tccctttagt gagggttaat tgcgcgcatg cccgacggcg aggatctcgt      2880
cgtgacccat ggcgatgcct gcttgccgaa tatcatggtg aaaatggcc gcttttctgg       2940 attcatcgac tgtggccggc tgggtgtggc ggaccgctat caggacatag cgttggctac      3000
ccgtgatatt gctgaagagc ttggcggcga atgggctgac cgcttcctcg tgctttacgg      3060
tatcgccgct cccgattcgc agcgcatcgc cttctatcgc cttcttgacg agttcttctg      3120
agcgggactc tggggttcga atgaccgac caagcgacgc ccaacctgcc atcacgagat       3180
ttcgattcca ccgccgcctt ctatgaaagg ttgggcttcg gaatcgtttt ccgggacgcc      3240
ggctggatga tcctccagcg cggggatctc atgctggagt tcttcgccca ccccaacttg      3300
tttattgcag cttataatgg ttacaaataa agcaatagca tcacaaattt cacaaataaa      3360 gcatttttt cactgcattc tagttgtggt ttgtccaaac tcatcaatgt atcttatcat       3420
gtctggatcc cgtcgacctc gagagcttgg cgtaatcatg gtcatagctg tttcctgtgt      3480
gaaattgtta tccgctcaca attccacaca acatacgagc cggaagcata agtgtaaag      3540 cctggggtgc ctaatgagtg agctaactca cattaattgc gttgcgctca ctgcccgctt     3600
tccagtcggg aaacctgtcg tgccagctgc attaatgaat cggccaacgc gcgggagag      3660 gcggtttgcg tattgggcgc tcttccgctt cctcgctcac tgactcgctg cgctcggtcg     3720
ttcggctgcg gcgagcggta tcagctcact caaaggcggt aatacggtta ccacagaat      3780 caggggataa cgcaggaaag aacatgtgag caaaaggcca gcaaaaggcc aggaaccgta    3840
aaaaggccgc gttgctggcg ttttccata ggctccgccc ccctgacgag catcacaaaa      3900
atcgacgctc aagtcagagg tggcgaaacc cgacaggact ataaagatac caggcgtttc     3960
cccctggaag ctccctcgtg cgctctcctg ttccgaccct gccgcttacc ggatacctgt     4020
ccgcctttct cccttcggga agcgtggcgc tttctcaatg ctcacgctgt aggtatctca    4080
gttcggtgta ggtcgttcgc tccaagctgg gctgtgtgca cgaaccccc gttcagcccg      4140 accgctgcgc cttatccggt aactatcgtc ttgagtccaa cccggtaaga cacgacttat    4200
cgccactggc agcagccact ggtaacagga ttagcagagc gaggtatgta ggcggtgcta     4260
cagagttctt gaagtggtgg cctaactacg gctacactag aaggacagta tttggtatct    4320
gcgctctgct gaagccagtt accttcggaa aaagagttgg tagctcttga tccggcaaac    4380
aaaccaccgc tggtagcggt ggtttttttg tttgcaagca gcagattacg cgcagaaaaa     4440
aaggatctca agaagatcct ttgatctttt ctacgggtc tgacgctcag tggaacgaaa      4500
actcacgtta agggatttg gtcatgagat tatcaaaaag gatcttcacc tagatccttt      4560
taaattaaaa atgaagtttt aaatcaatct aaagtatata tgagtaaact tggtctgaca    4620
gttaccaatg cttaatcagt gaggcaccta tctcagcgat ctgtctattt cgttcatcca    4680
tagttgcctg actccccgtc gtgtagataa ctacgatacg ggagggctta ccatctggcc    4740
ccagtgctgc aatgatacg cgagacccac gctcaccggc tccagattta tcagcaataa     4800
accagccagc cggaagggcc gagcgcagaa gtggtcctgc aactttatcc gcctccatcc    4860
```

-continued

| | | | | | |
|---|---|---|---|---|---|
|agtctattaa|ttgttgccgg|gaagctagag|taagtagttc|gccagttaat|agtttgcgca 4920|
|acgttgttgc|cattgctaca|ggcatcgtgg|tgtcacgctc|gtcgtttggt|atggcttcat 4980|
|tcagctccgg|ttcccaacga|tcaaggcgag|ttacatgatc|ccccatgttg|tgcaaaaaag 5040|
|cggttagctc|cttcggtcct|ccgatcgttg|tcagaagtaa|gttggccgca|gtgttatcac 5100|
|tcatggttat|ggcagcactg|cataattctc|ttactgtcat|gccatccgta|agatgctttt 5160|
|ctgtgactgg|tgagtactca|accaagtcat|tctgagaata|gtgtatgcgg|cgaccgagtt 5220|
|gctcttgccc|ggcgtcaata|cgggataata|ccgcgccaca|tagcagaact|ttaaaagtgc 5280|
|tcatcattgg|aaaacgttct|tcggggcgaa|aactctcaag|gatcttaccg|ctgttgagat 5340|
|ccagttcgat|gtaacccact|cgtgcaccca|actgatcttc|agcatctttt|actttcacca 5400|
|gcgtttctgg|gtgagcaaaa|acaggaaggc|aaaatgccgc|aaaaaaggga|ataagggcga 5460|
|cacggaaatg|ttgaatactc|atactcttcc|tttttcaata|ttattgaagc|atttatcagg 5520|
|gttattgtct|catgagcgga|tacatatttg|aatgtattta|gaaaaataaa|caaatagggg 5580|
|ttccgcgcac|atttccccga|aaagtgccac|ctgacgtc| |5618|